US007268240B2

(12) United States Patent
Romanczyk, Jr. et al.

(10) Patent No.: US 7,268,240 B2
(45) Date of Patent: Sep. 11, 2007

(54) SYNTHETIC METHODS FOR POLYPHENOLS

(75) Inventors: Leo J. Romanczyk, Jr., Hackettstown, NJ (US); Alan P. Kozikowski, Princeton, NJ (US); Werner Tueckmantel, Washington, DC (US); Marc E. Lippman, Bethesda, MD (US)

(73) Assignee: Mars, Inc.

( * ) Notice: Subject to any disclaimer, the term of this patent is extended or adjusted under 35 U.S.C. 154(b) by 307 days.

(21) Appl. No.: 10/858,449

(22) Filed: May 28, 2004

(65) Prior Publication Data

US 2004/0236123 A1    Nov. 25, 2004

Related U.S. Application Data

(60) Continuation of application No. 10/355,606, filed on Jan. 31, 2003, now Pat. No. 6,849,746, which is a division of application No. 10/017,812, filed on Dec. 14, 2001, now Pat. No. 6,528,664, which is a continuation-in-part of application No. 08/948,226, filed on Oct. 9, 1997, now Pat. No. 6,207,842.

(51) Int. Cl.
C07D 311/62       (2006.01)
(52) U.S. Cl. ..................................... 549/399
(58) Field of Classification Search ................. 549/399
See application file for complete search history.

(56) References Cited

U.S. PATENT DOCUMENTS 4,255,336 A    3/1981   Albert et al. ............. 260/345.2
4,644,011 A    2/1987   Ballenegger et al. ....... 514/456
5,554,645 A    9/1996   Romanczyk, Jr. et al. .. 514/453
6,156,912 A   12/2000   Tuckmantel et al. ........ 549/399
6,207,842 B1   3/2001   Romanczyk et al. ....... 549/399
6,420,572 B1   7/2002   Romanczyk et al. ....... 549/400
6,476,241 B1  11/2002   Kozikowski et al. ....... 549/399
6,528,664 B2   3/2003   Romanczyk et al. ....... 549/400
6,720,432 B2   4/2004   Kozikowski et al. ....... 549/415
2003/0114691 A1 6/2003  Romanczyk et al. ....... 549/354
2003/0176620 A1 9/2003  Romanczyk et al. ......... 528/86
2004/0116718 A1 6/2004  Kozikowski et al. ....... 549/403
2004/0176441 A1 9/2004  Romanczyk et al. ....... 514/456

FOREIGN PATENT DOCUMENTS

DE          EP 0039844       11/1978

(Continued)

OTHER PUBLICATIONS

U.S. Appl. No. 09/292,244, filed Apr. 15, 1999, Basak et al.

(Continued)

*Primary Examiner*—Bernard Dentz
(74) *Attorney, Agent, or Firm*—Margaret B. Kelley; Gibbons, P.C.

(57) ABSTRACT

A process is disclosed for the production of polyphenol oligomers having n polyphenol monomeric units, n being an integer from 2-18. The process includes coupling of a protected polyphenol, having protected phenolic hydroxyl groups, with a C-4 functionalized polyphenol monomer. The protected polyphenol may be a protected polyphenol monomer or a protected polyphenol oligomer having 2-17 monomeric units. Advantageously, polyphenol monomeric units forming the polyphenol oligomers may be the same or different flavanoid compounds.

14 Claims, 4 Drawing Sheets

FOREIGN PATENT DOCUMENTS

| EP | DE 15 18 003.7 | 1/1969 |
|----|----------------|--------|
| EP | 0096 007 | 5/1983 |
| EP | 0216 936 | 4/1987 |
| JP | 41 90774 | 11/1990 |
| WO | WO90/13304 | 11/1990 |
| WO | WO97/36597 A | 10/1997 |

OTHER PUBLICATIONS

U.S. Appl. No. 10/481,729, filed Dec. 22, 2003, Kozikowski et al.
U.S. Appl. No. 10/783,801, filed May 28, 2004, Kozikowski et al.
Balde, A.M. et al., Phytochemistry, vol. 30, No. 12. p. 4129-4135 (1991).
Botha, J.J. et al., *J. Chem. Soc.* Perkin I, 1235-1245 (1981).
Botha, J.J. et al, *J. Chem. Soc.* Perkin I, 527-533 (1982).
Buffnoir et al., Third Tannin Conference Bend Oregon, pp. 15-16 (1998).
Chu, S.C. et al, *J. of Natural Products*, 55, (2), 179-183 (1992).
Delcour, J.A. et al, *J. Chem. Soc.* Perkin Trans I 1711-1717 (1983).
Deschner, E.E. et al, Carcinogenesis, 7, 1193-1196, (1991).
Dess et al., J. Am. Chem. Soc. vol. 113, pp. 7277-7287 (1991).
Ferriera, D. et al, Tetrahedron, 48, (10), 1743-1803 (1992).
Foo, L.Y. et al, *J. Chem. Soc.* Perkin I 1983:1535-1543.
Foo, L.Y. et al, *J. Chem. Soc.*, Chem. Commun., 85-86 (Sep. 1984).
Funayama, M. et al, *Biosci. Biotech. Biochem.*, 58, (5), 817-821 (1994).
Ho, C.T., Lee C.Y., and Huang, M.T. Eds., Phenolic Compounds in Foods and Their Effects on Health I. Analysis, Occurrence and Chemistry, ACS Symposium Series 506, American Chemical Society, Washington D.C. (1992).
Hundt, H.K. et al, *J. Chem. Soc.* Perkin I: 1227-1234 (1981).
Ireland et al., J. Org. Chem , vol. 58, p. 2899 (1993).
Kato, R. et al, Carcinogenesis, 1301-1305 (1983).
Kawamoto, H, et al. Synthetic Communications, 26(3), 531-534 (1996).
Kawamoto, H. et al, Mokazai gakkaishi, 37, (5) 488-493 (1991).
Keogh et al, Chem. Ind. (London) 2100-1 (1961). Abstract only.
Khanbabaee, K. et al, Tetrahedron, 53:31, 10725-10732 (1997).
Kiatgrajai P., et al. *J. Org. Chem.* 47, 2910-2012 (1982).

Kitao et al, *Biosci. Biotech. Biochem.* 59(11), 2167-2169, (1995).
Kolodziej, H., Phytotherapy Research, 9:410-415 (1995).
Kozikowski et al., "Studies in Polyphenol Chemistry and Bioactivity. 3.[1,2] Stereocontrolled Synthesis of Epicatechin-4α,8-epicatechin, an Unnatural Isomer of the B-Type Procyanidins", J. Org. Chem., 2001.
Kozikowski, A, et al. J. Org. Chem., 65, 5371-5381 (2000).
Meyer, S., *J. Org. Chem.*, 59: 7549-7552 (1994).
Mirura, et al., Radioisotopes, vol. 32, No. 5 pp. 225-230 (1983).
Newman, R.H., Magnetic Resonance in Chemistry 25:118-124 (1987).
Nonaka G-I., *Chem. Pharm. Bull.* 31 (11) 3906-3914 (1983).
Nonaka G-I., et al. *J. Chem. Soc.* Perkin Trans., I: p. 2139-2145 (1983).
Okuda, T. et al, Molecular Structures and Pharmacological activities of Polyphenols—Oligomeric Hydrolyzable Tannins and Others—Presented at the XVIth International Conference of the Groupe Polyphenols, Lisbon, Portugal, Jul. 13-16, 1992.
Ozanne, et al., Organic Letters, vol. 5 No. 16 pp. 2903-2906.
Pierre. M.C. et al. Tetrahedron Letters 38, (32), 5639-5642 (1997).
Porter, L.J. "Flavans and Proanthocyanidins" from "The Flavonoids" Ed. J.B. Harborne, Chapmen and Hall Ltd., p. 21-62 (1988).
Roux & Ferreira, Fortschritte d. Chemie Org. Naturst., pp. 47-76 (1982).
Roux, D.G. et al, *J. Agric. Food Chem.* 28:216-222 (1980).
Saito, Akiko et al., "Synthetic Studies of Proanthocyanidins. Highly Stereoselective Synthesis of the Catechin Dimer, Procyanidin-B3", Biosci. Bioetechnol. Biochem., 66(8), 1764-1767, 2002.
Steenkamp et al, Tetrahedron letters, 26, (25) 3045-3048 (1985).
Steynberg, P.J. et al, Tetrahedron 54:8153-8158 (1998).
Takashi Tanaka et al. Phytochemistry, vol. 53 pp. 311-316 (2000).
Toshima, K., Tatsuta, K., *Chem. Rev.*, 93, 1503-1531 (1993).
Tuckmantel Werner et al., J. Am. Chem. Soc. 1999, 121, 12073-12081.
Weinges, K. et al. *Chem. Ber.* 103, 2344-2349 (1970).
Saito, et al., "Synthetic Studies of Proanthocyanidins. Part 2: Stereoselective gram-scale synthesis . . . " Tetrahedron Letters (2002) 58:7829-7837.

SYNTHETIC METHODS FOR POLYPHENOLS

This application is a continuation of Ser. No. 10/355,606 filed Jan. 31, 2003 now U.S. Pat. No. 6,849,746 issued Feb. 1, 2005, which is a division of Ser. No. 10/017,812 flied Dec. 14, 2001 now U.S. Pat. No. 6,528,664 issued Mar. 4, 2003, which is a continuation of Ser. No. 09/169,554 filed Oct. 9, 1998 now U.S. Pat. No. 6,420,572 issued Jul. 16, 2002, which is a continuation-in-part of Ser. No. 08/948,226 filed Oct. 9, 1997 now U.S. Pat. No. 6,207,842 issued Mar. 27, 2001.

BACKGROUND OF THE INVENTION

1. Field of the Invention

This invention relates to synthetic polyphenol monomers and oligomers, derivatives thereof, and methods for making and using the same.

2. Related Background Art

Polyphenols are a highly diverse group of compounds (Ferreira, D., Steynberg, J. P., Roux, D. G. and Brandt, E. V., Tetrahedron, 48, (10), 1743-1803 (1992)) which widely occur in a variety of plants, some of which enter into the food chain. In many cases, they represent an important class of compounds present in the human diet. Although some of the polyphenols are considered to be non-nutritive, interest in these compounds has arisen because of their possible beneficial effects on health.

For instance, quercetin (a flavonoid) has been shown to possess anticarcinogenic activity in experimental animal studies (Deschner, E. E., Ruperto, J., Wong, G. and Newmark, H. L., Carcinogenesis, 7, 1193-1196 (1991) and Kato, R., Nakadate, T., Yamamoto, S. and Sugimura, T., Carcinogenesis, 4, 1301-1305 (1983)). (+)-Catechin and (−)-epicatechin (flavan-3-ols) have been shown to inhibit Leukemia virus reverse transcriptase activity (Chu S.-C., Hsieh, Y.-S. and Lim, J.-Y., J. of Natural Products, 55, (2), 179-183 (1992)). Nobotanin (an oligomeric hydrolyzable tannin) has also been shown to possess anti-tumor activity (Okuda T., Yoshida, T., and Hatano, T., Molecular Structures and Pharmacological Activities of Polyphenols—Oligomeric Hydrolyzable Tannins and Others—Presented at the XVIth International Conference of the Groupe Polyphenols, Lisbon, Portugal, Jul. 13-16, 1992). Statistical reports have also shown that stomach cancer mortality is significantly lower in the tea producing districts of Japan. Epigallocatechin gallate has been reported to be the pharmacologically active material in green tea that inhibits mouse skin tumors (Okuda et al., ibid.). Ellagic acid has also been shown to possess anticarcinogen activity in various animal tumor models (Boukharta M., Jalbert, G. and Castonguay, A., Efficacy of Ellagitannins and Ellagic Acid as Cancer Chemopreventive Agents—Presented at the XVIth International Conference of the Groupe Polyphenols, Lisbon, Portugal, Jul. 13-16, 1992). Proanthocyanidin oligomers have been disclosed (JP 4-190774) by the Kikkoman Corporation for use as antimutagens. The use of phenolic compounds in foods and their modulation of tumor development in experimental animal models has been recently presented at the 202nd National Meeting of The American Chemical Society (Phenolic Compounds in Foods and Their Effects on Health I, Analysis, Occurrence & Chemistry, Ho, C.-T., Lee, C. Y., and Huang, M.-T editors, ACS Symposium Series 506, American Chemical Society, Washington, D.C. (1992); Phenolic Compounds in Foods and Their Effects on Health II. Antioxidants & Cancer Prevention, Huang, M.-T., Ho, C.-T., and Lee, C. Y. editors, ACS Symposium Series 507, American Chemical Society, Washington, D.C. (1992)).

Procyanidin polyphenols, and particularly higher oligomers thereof, have recently been found to possess a broad spectrum of biological activity Reference is made to U.S. patent application Ser. No. 08/709,406 filed Nov. 6, 1996, now U.S. Pat. No. 6,015,913 issued Jan. 18, 2000 and U.S. application Ser. No. 08/317,226 filed Oct. 3, 1994, now U.S. Pat. No. 5,554,645 issued Sep. 10, 1996, each of which is incorporated herein by reference. These patents disclose a variety of health benefits provided by procyanidin polyphenols as well as a means of increasing the concentration of these beneficial polyphenols in extracts, foods, pharmaceutical preparations and chocolate compositions. Reference is also made to parent U.S. application Ser. No. 08/948,226 filed Oct. 9, 1997, now U.S. Pat. No. 6,207,842 issued Mar. 27, 2001, which discloses methods of preparing polyphenol oligomers, and specifically procyanidin polyphenols, the disclosure of which is also incorporated herein by reference.

Isolation, separation, purification, and identification methods have been established for the recovery of a range of procyanidin oligomers for comparative in vitro and in vivo assessment of biological activities. For instance, anti-cancer activity is elicited by pentameric through decameric procyanidins, but not by monomers through tetrameric compounds. Currently, gram quantities of pure (>95%) pentamer are obtained by time-consuming methods which are not satisfactory for obtaining a sufficient quantity of the pentamer for large scale pharmacological and bioavailability studies. Even greater effort is required to obtain gram quantities of higher oligomers, hexamers through dodecamers, for similar studies since they are present in the natural product in much lower concentrations than the pentamer. Additionally, increasing oligomeric size increases structural complexity. Factors such as differences in the chirality of the monomeric units comprising the oligomer, different interflavan bonding sites, differences in the chirality of the interflavan bonding, dynamic rotational isomerization of the interflavan bonds, and the multiple points of bonding at nucleophilic centers pose efficiency constraints on current analytical methods of separation and purification for subsequent identification.

These collective factors point to a need for synthesis methods to permit the unambiguous proof of both structure and absolute configuration of higher oligomers, to provide large quantities of structurally defined oligomers for in vitro and in vivo assessment and to provide novel structural derivatives of the naturally occurring procyanidins to establish the structure-activity relationships of these materials. Accordingly, it would be advantageous to develop a versatile synthetic process capable of providing large quantities of any desired polyphenol oligomer.

SUMMARY OF THE INVENTION

This invention is directed to a process for preparing a polyphenol oligomer comprised of coupled polyphenol monomeric, or flavanoid units. The process of this invention comprises:

(a) protecting each phenolic hydroxyl group of a polyphenol monomer with a protecting group to form a protected polyphenol monomer having the formula:

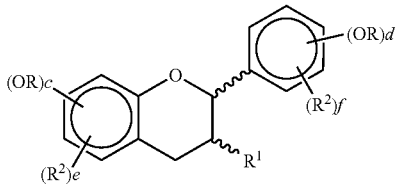

wherein
c is an integer from 1 to 3;
d is an integer from 1 to 4;
e is an integer from 0 to 2;
f is an integer from 0 to 2;
$R^1$ is H, OH, or $OR^3$;
R and $R^3$ are independently protecting groups; and
$R^2$ halo;

(b) functionalizing the 4-position of at least one protected polyphenol monomer to form a functionalized, protected polyphenol monomer having the formula:

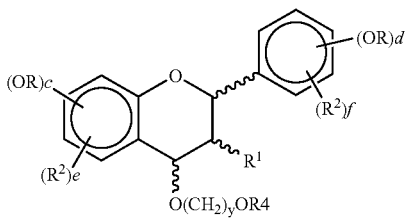

wherein
c is an integer from 1 to 3;
d is an integer from 1 to 4;
e is an integer from 0 to 2;
f is an integer from 0 to 2;
y is an integer from 2 to 6;
$R^1$ is H, OH, or $OR^3$;
$R^4$ is H or $R^5$
R, $R^3$, and $R^5$ are independently protecting groups; and
$R^2$ is halo;

(c) coupling the protected polyphenol monomer with the functionalized, protected polyphenol monomer to form a protected polyphenol dimer, wherein the polyphenol monomeric units of the protected polyphenol monomer and the functionalized, protected polyphenol monomer are the same or different; and (d) optionally repeating the functionalizing and coupling steps to form a polyphenol oligomer having in monomeric units, where n is 3 to 18. The halo group(s) of $R^2$, when e+f is at least 2, may be the same or different and may be selected from the group consisting of chloro, fluoro, bromo, and iodo.

The process of this invention also provides for the preparation of novel derivatives of the polyphenol oligomer. Halogenation of the functionalized, protected polyphenol monomer provides a halogenated, functionalized polyphenol monomer having the formula:

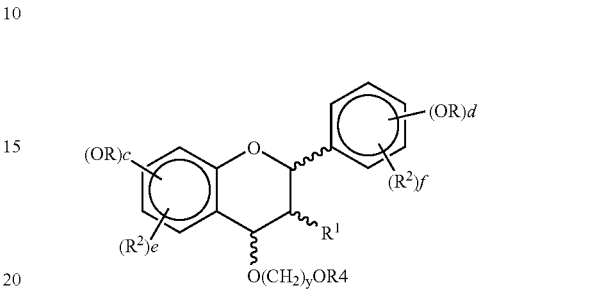

wherein, c is 1 to 3; d is 1 to 4; e is 0 to 2; f is 0 to 2; y is 2 to 6; R' is H, OH, or $OR^3$; $R^4$ is H or $R^5$; R, $R^3$, and $R^5$ are independently protecting groups; and $R^2$ is a halo wherein, if e+f is at least 2, the halo substituents may be the same or different. This halogenated, functionalized monomer may be used for the preparation of a halogenated polyhphenol oligomer by coupling this monomer with either a protected polyphenol monomer or with a protected polyphenol oligomer. Alternatively, halogentated polyphenol oligomers may be prepared by direct halogentation of the polyphenol oligomer.

Other novel derivatives may be prepared by esterifying or glycosylating the polyphenol oligomer to produce a derivatized polyphenol oligomer. Formation of the derivatized oligomers may be conducted either prior to or subsequent to removal of the protecting groups from the phenolic hydroxyl groups of the polyphenol oligomer. Accordingly, this invention is also directed to novel polyphenol monomers, novel polyphenol oligomers, and novel derivatized polyphenol monomers and oligomers.

DETAILED DESCRIPTION OF THE INVENTION

Figure 1A:
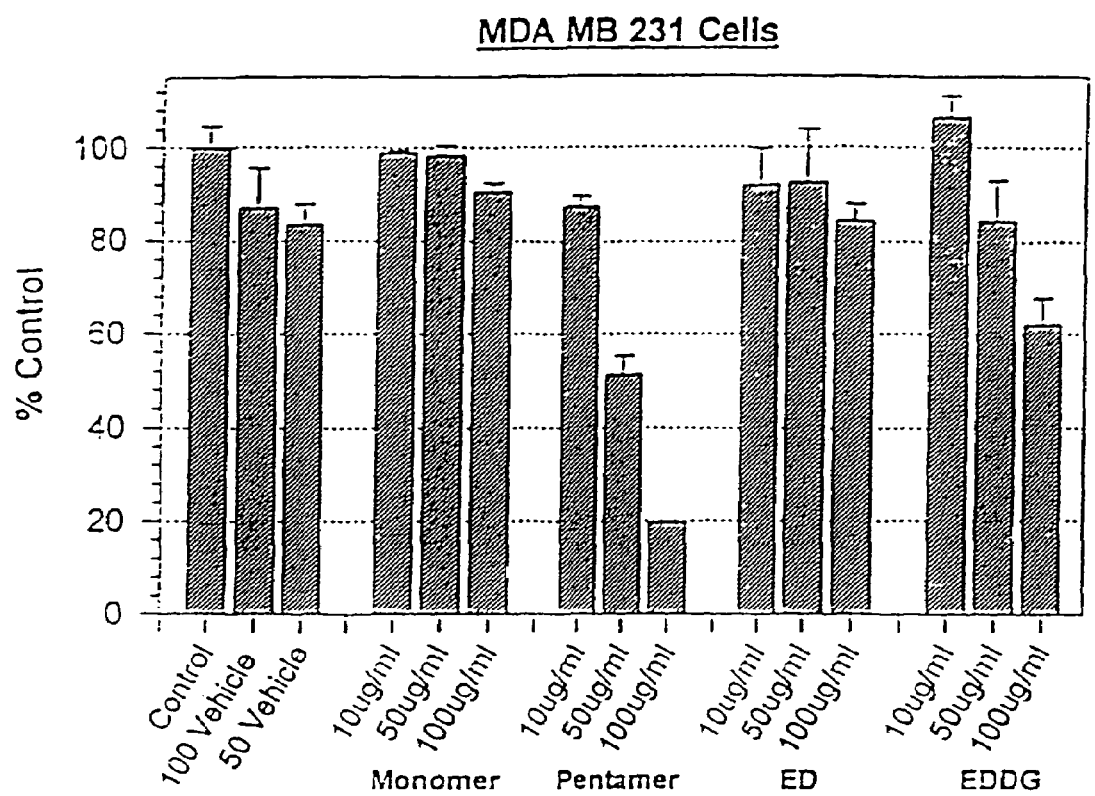
FIG. 1(a) is a bar graph showing the dose-response relationship between the control (solvent vehicle), monomer (epicatechin), pentamer (purified by preparative HPLC), ED "synthetic epicatechin dimer (EC-(4β→8)-EC)), and EDDG (synthesized epicatechin dimer bisgallate (EC-3-O-galloyl-(4β→8)-EC-3-O-gallate) against the human breast cancer cell line MDA MB 231 at various µg/mL concentrations.

The present invention relates to a process for synthesizing polyphenol oligomers and derivatives thereof. The subject compounds of the invention have the same uses, and are formulated, purified, and administered in the same manner as described in Ser. No. 08/831,245 filed Apr. 2, 1997, now U.S. Pat. No. 6,297,273 issued Oct. 2, 2001. Accordingly, the compounds of this invention may be used, for example, as antineoplastic agents, antioxidants, DNA topoisomerase II enzyme inhibitors, cyclo-oxygenase and/or lipoxygenase modulators, nitric oxide or nitric oxide-synthase modulators, as non-steroidal anti-flammatory agents, antimicrobial agents, apoptosis modulators, platelet aggregation modulators, glucose modulators, and inhibitors of oxidative DNA damage.

As used herein, the term polyphenol monomer means a polyhydroxy-substituted compound having the following flavanoid based structure:

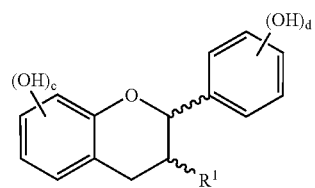

wherein c is an integer from 1 to 3;

d is an integer from 1 to 4;

$R^1$ is H or OH.

The polyphenol monomer may contain additional substituents, or derivatives of the hydroxyl substituents, as described below. The term polyphenol oligomer means a polymer composed of a series of polyphenol monomeric units that may possess the same or different flavanoid structures. The polyphenol monomeric units are the polyphenol monomers that have been coupled or bonded together to form an oligomer. The term polyphenol(s) includes proanthocyanidins, and derivatives thereof, and specifically includes procyanidins, such as those that can be extracted from cocoa beans, and derivatives thereof, as well as structurally similar synthetic materials.

Representative proanthocyanidins include:

|  |  | Substitution Pattern |  |  |  |  |  |  |
|---|---|---|---|---|---|---|---|---|
| Class | Monomer | 3 | 5 | 7 | 8 | 3' | 4' | 5' |
| Proapigeninidin | Apigeniflavan | H | OH | OH | H | H | OH | H |
| Proluteolinidin | Luteoliflavan | H | OH | OH | H | OH | OH | H |
| Protricetinidin | Tricetiflavan | H | OH | OH | H | OH | OH | OH |
| Propelargonidin | Afzelechin | OH | OH | OH | H | H | OH | H |
| Procyanidin | Catechin | OH | OH | OH | H | OH | OH | H |
| Prodelphinidin | Gallocatechin | OH | OH | OH | H | OH | OH | OH |
| Proguibourtinidin | Guibourtinidol | OH | H | OH | H | H | OH | H |
| Profisetinidin | Fisetinidol | OH | H | OH | H | OH | OH | H |
| Prorobinetinidin | Robinetinidol | OH | H | OH | H | OH | OH | OH |
| Proteracacinidin | Oritin | OH | H | OH | OH | H | OH | H |
| Promelacacinidin | Prosopin | OH | H | OH | OH | OH | OH | H |

The present invention provides a process of preparing substantially pure polyphenol oligomers, and derivatives thereof.

In a preferred embodiment, the present invention provides a process of synthesizing polyphenol oligomers of the formula:

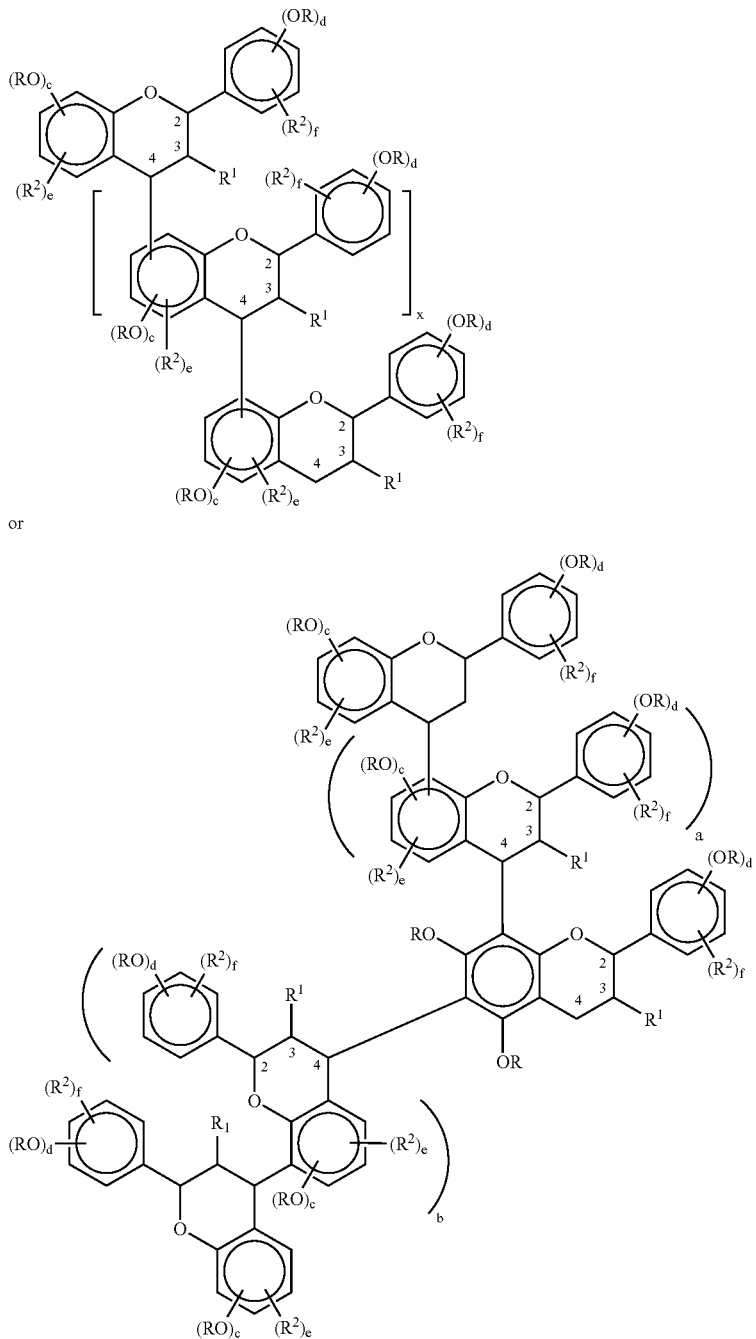

wherein
x is an integer from 0 to 16;
a is an integer from 1 to 15;
b is an integer from 1 to 15;
the sum a+b is an integer from 2 to 17;
c is independently an integer from 1 to 3;
d is independently an integer from 1 to 4;
e is independently an integer from 0 to 2;
f is independently an integer from 0 to 2;
R is independently hydrogen, $C_1$-$C_4$ alkyl, benzyl, substituted benzyl, or a silyl moiety containing $C_1$-$C_6$ alkyl or aryl substituents, or, when c or d is 2 and are adjacent, methylene, diphenylmethylene or substituted diphenylmethylene, wherein said substituted benzyl or each substituted phenyl may contain substituents selected from the group consisting of halo, nitro, cyano, aryl, $C_1$-$C_6$ alkyl, $C_1$-$C_6$ haloalkyl, $C_1$-$C_6$ alkoxy $C_1$-$C_6$ haloalkoxy, $C_3$-$C_8$ cycloalkyl, $C_3$-$C_8$ cycloalkoxy; and $R^1$ is hydrogen, hydroxy, an —O-glycoside, an —O-substituted glycoside, —OC(O)-aryl, —OC(O)-substituted aryl, —OC(O)-styryl, or —OC(O)-substituted styryl; wherein the substituted glycoside is substituted by —C(O)-aryl, —C(O)-substituted aryl, —C(O)-styryl, or —C(O)-substituted styryl; wherein said substituted aryl or substituted styryl may contain the substituents selected from the group consisting of halo, hydroxyl, nitro, cyano, aryl, amino, methylenedioxy, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, and $C_3$-$C_8$ cycloalkoxy; $R_2$ is halo; and $R^2$ is halo, wherein if e+f is at least 2 the halo substituent may be the same or different; and wherein said process comprises the steps of subjecting a first polyphenol monomer to conditions sufficient to produce a C-4 functionalized polyphenol monomer and coupling that C-4 functionalized monomer with a second polyphenol monomer or an oligomer having up to 17 monomeric units that are the same or different. The first and second polyphenol monomers may be the same or different.

The process of the present invention may be used to prepare substantially pure polyphenol oligomers, and derivatives thereof. The oligomeric compounds are comprised of n polyphenol monomeric units, wherein n is an integer of 2 through 18, preferably 2 through 5, or 4 through 12, more preferably n is 3 through 12, and most preferably n is 5 through 12, and having linkages of 4→6 and 4→8. The polyphenol oligomers prepared by the processes of this invention may be represented by the formula above, wherein x is 0 through 16, and higher. When x is 0, the oligomer is termed a "dimer"; when x is 1, the oligomer is termed a "trimer"; when x is 2, the oligomer is termed a "tetramer"; when x is 3, the oligomer is termed a "pentamer"; and similar recitations may be designated for oligomers having x up to and including 16 and higher, such that when x is 16, the oligomer is termed an "octadecamer".

Linear and branched polyphenol oligomers may be prepared by the process of the present invention using a sequence of reaction comprising protecting, functionalizing, coupling, and deprotecting. In each reaction sequence, any polyphenol monomer, as exemplified above, may be used to prepare linear or branched oligomers containing monomeric units of the same polyphenol monomer or of different polyphenol monomers. Higher oligomers may be prepared by repeating the coupling step by coupling a dimer, trimer, or higher oligomer with additional monomer.

Generally, the process for the production of polyphenol oligomers comprises the steps of:
  (a) protecting each phenolic hydroxyl group of at least a first and second polyphenol monomer using a suitable phenol protecting group to provide at least a first and a second protected polyphenol monomer, wherein the first and second polyphenol monomers may be the same or different flavanoid compounds;
  (b) functionalizing the 4-position of the first protected polyphenol monomer to produce a functionalized polyphenol monomer;
  (c) coupling the functionalized polyphenol monomer with the second protected polyphenol monomer to produce the polyphenol oligomer, wherein the oligomer is a protected polyphenol dimer.

The polyphenol dimer thus produced is composed of coupled first and second monomers. The functionalizing and coupling steps may be repeated to form polyphenol oligomers where the oligomers may be comprised of n monomers and where n is an integer from 3 to 18. Preferably, n is an integer from 5 to 12.

Accordingly, the process described above may be continued by:
  (a) functionalizing the 4-position of a third protected polyphenol monomer to form a third functionalized polyphenol monomer;
  (b) coupling the functionalized third polyphenol monomer with the protected polyphenol dimer to form a protected polyphenol trimer;
  (c) optionally repeating the functionalizing and coupling steps to form a polyphenol oligomer comprised of n monomers, wherein n is an integer from 3 to 18. The first, second and third polyphenol monomers may possess the same or different flavanoid structures.

Suitable protecting groups used in the process of this invention include those protecting groups that may be introduced and removed from the polyphenol monomers and oligomers without racemization or degradation of the monomers or oligomers and that are stable to the conditions used for functionalizing and coupling reactions. Methods for protecting and de-protecting hydroxyl groups are well known to those skilled in the art and are described in "Protective Groups in Organic Synthesis" T. W. Greene, John Wiley & Sons. Preferably, the protecting groups used in the process of this invention to protect the phenolic hydroxyl groups of the polyphenol monomers include benzyl, $C_1$-$C_4$ alkyl, substituted benzyl, alkyl silyl, aryl silyl, or substituted aryl silyl containing $C_1$-$C_6$ alkyl, aryl or substituted aryl substituents, wherein the substituted benzyl protecting group or substituted aryl may contain substituents selected from the group consisting of halo, nitro, cyano, aryl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, and $C_3$-$C_8$ cycloalkoxy. When the polyphenol monomer contains two phenolic hydroxyl groups that are adjacent, the protecting group may be methylene, diphenylmethylene or substituted diphenylmethylene, wherein each of the substituted phenyl groups of the diphenylmethylene protecting group may contain substituents selected from the group consisting of halo, nitro, cyano, aryl, $C_1$-$C_6$ alkyl, $C_1$-$C_6$ haloalkyl, $C_1$-$C_6$ alkoxy $C_1$-$C_6$ haloalkoxy, $C_3$-$C_8$ cycloalkyl, and $C_3$-$C_8$ cycloalkoxy.

As used herein, aryl means an aromatic hydrocarbon compound selected from the group consisting of phenyl, substituted phenyl, naphthyl, or substituted naphthyl, wherein the substituted phenyl or substituted naphthyl may contain substituents selected from the group consisting of halo, nitro, cyano, aryl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, and $C_3$-$C_8$ cycloalkoxy.

The protecting group may be removed from the phenolic hydroxyl groups of the polyphenol oligomer to produce an unprotected polyphenol oligomer. In addition, the protected or unprotected polyphenol oligomer may be derivatized to produce derivatized polyphenol oligomers.

Preferably, the process of the present invention comprises:
  (a) protecting each phenolic hydroxyl group of a first and second polyphenol monomer using a suitable phenol protecting group to form a first and a second protected polyphenol monomer, wherein the first and second polyphenol monomers may be the same or different flavanoid compounds;
  (b) oxidatively functionalizing the 4-position of the first protected polyphenol monomer using an oxidizing agent to provide a 4-functionalized protected polyphenol monomer;
  (c) coupling the protected polyphenol monomer and the functionalized, protected polyphenol monomer using a catalyst to provide a polyphenol oligomer; and
  (d) optionally deprotecting the polyphenol oligomer to provide an unprotected polyphenol oligomer.

The oxidative functionalization of the 4-position of a protected polyphenol monomer produces a functionalized protected polyphenol monomer having the formula:

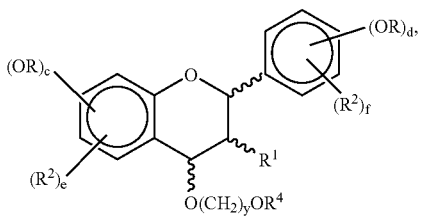

wherein
c is an integer from 1 to 3;
d is an integer from 1 to 4;
e is an integer from 0 to 2;
f is an integer from 0 to 2;
y is an integer from 2 to 6;
$R^1$ is H, OH or $OR^3$;
$R^4$ is H or $R^5$;
R, $R^3$ and $R^5$ are independently protecting groups; and
$R^2$ is halo.

When e or f are 1 or 2, functionalization of the monomer preferably precedes introduction of the halo substituent.

An important transformation in the process of the present invention is the formation of the oxidatively functionalized protected polyphenol monomer used in the oligomer-forming coupling reaction. It has been determined that high purity of this monomer is important for obtaining oligomeric products in good purity. Advantageously, it has been discovered that formation of the 4-alkoxy polyphenol monomer using ethylene glycol, in place of lower alkyl alcohols, provides a functionalized polyphenol monomer that may be readily purified by chromatography. Use of methanol, ethanol, or even isopropyl alcohol, provides 4-alkoxy polyphenol monomers that are not separable or difficult to separate chromatographically from the non-oxidized phenol and from by-products and cannot be used satisfactorily in the oligomer-forming coupling reaction. Accordingly, another aspect of the present invention comprises providing a substantially pure 4(2-hydroxyethyl) functionalized polyphenol monomer useful for forming polyphenol oligomers. A preferred quinone-type oxidizing agent is 2,3-dichloro-5,6-dicyano-1,4-benzoquinone (DDQ).

Another important transformation in the process of this invention is the coupling of the oxidatively functionalized polyphenol monomer to a protected polyphenol monomer or a protected polyphenol oligomer. The coupling reaction is conducted using a protic acid catalyst or a Lewis acid catalyst. Hydrochloric acid (HCl) is an exemplary protic acid that may be used as a catalyst in the process of this invention. A particularly useful form of hydrochloric acid is as an anhydrous solution in dioxane. Exemplary Lewis Acid catalysts that are useful in the present invention include titanium tetrahalides (e.g. titanium tetrachloride), aluminum trihalides (e.g. aluminum trichloride), boron trihalides. (e.g. boron trifluoride etherate), trialkyl or triaryl silyl compounds (e.g. trimethyl silyl triflate) and the like.

Exemplary oxidizing agents useful in the process of this invention include quinone-type oxidizing agents and metal acetate oxidizing agents (e.g. lead tetraacetate).

Preferably, the process of the present invention comprises:
(a) protecting each phenolic hydroxyl group of a first and a second polyphenol monomer using a benzyl ether protecting group to produce a first and a second protected polyphenol monomer, wherein the first and second polyphenol monomers may be the same or different;
(b) oxidatively functionalizing the 4-position of the first protected polyphenol monomer using a quinone oxidizing agent in the presence of an alcohol, preferably a diol, to provide a 4-alkoxy functionalized, protected polyphenol monomer having the formula:

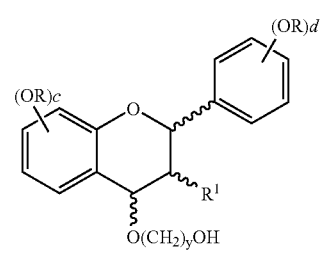

wherein
c is an integer from 1 to 3;
d is an integer from 1 to 4;
y is an integer from 2 to 6;
R is a protecting group; and
$R^1$ is H or OH;
(c) coupling the second protected polyphenol monomer and the functionalized polyphenol monomer using a protic acid catalyst or a Lewis acid catalyst to form a protected polyphenol oligomer; and
(d) deprotecting the protected polyphenol oligomer to form an unprotected polyphenol oligomer.

More preferably, the process of the present invention comprises:
(a) protecting each phenolic hydroxyl group of a first and a second polyphenol monomer using a benzyl ether protecting group to produce a first and a second protected polyphenol monomer;
(b) oxidatively functionalizing the 4-position of the second protected polyphenol monomer using 2,3-dichloro-5,6-dicyano-1,4-benzoquinone in the presence of ethylene glycol to provide a 4-functionalized protected polyphenol monomer having the formula:

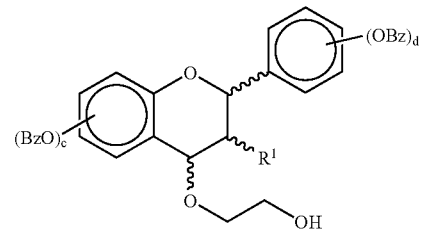

wherein
c is an integer from 1 to 3;
d is an integer from 1 to 4;
$R^1$ is H or OH; and
Bz represents a benzyl moiety (c) coupling the protected polyphenol monomer and the functionalized, protected polyphenol monomer using titanium tetrachloride to form a protected polyphenol dimer; and (d) deprotecting the protected polyphenol dimer to form an unprotected polyphenol dimer.

The processes of this invention also provides for the preparation of novel derivatized oligomers, wherein at least one unprotected hydroxyl group of the polyphenol oligomer is derivatized using standard esterification or glycosylation techniques to form an ester or glycosyl ether derivative, respectively. Accordingly, this invention is directed to a process for the production of a derivatized polyphenol oligomer, which comprises esterifying a protected polyphenol oligomer, wherein each phenolic hydroxyl group of the polyphenol oligomer is protected, to produce a protected esterified polyphenol oligomer, and to a process which comprises esterifying an unprotected polyphenol oligomer to produce an esterified polyphenol oligomer. Optionally, the protecting groups of the protected esterified polyphenol oligomer may be removed to provide an esterified polyphenol oligomer. This invention is also directed to a process for the production of a derivatized polyphenol oligomer, which comprises glycosylating the polyphenol oligomer, that is forming a glycosyl ether derivative of the oligomer, wherein each phenolic hydroxyl group of the polyphenol oligomer is protected, to produce a protected glycosylated polyphenol oligomer, and to a process which comprises glycosylating an unprotected polyphenol oligomer to produce a glycosylated polyphenol oligomer. Optionally, the protecting groups of the protected glycosylated polyphenol oligomer may be removed to provide a glycosylated polyphenol oligomer. In addition, ester derivatives of the glycosyl ethers may be prepared by esterifying at least one hydroxyl group of the glycosyl moiety.

Polyphenol oligomer ester derivatives may be prepared by treatment of the oligomer having a reactive hydroxyl moiety with an activated acid. As used herein, an activated acid is an organic acid having a carboxyl moiety that is activated toward reaction with an hydroxyl moiety. The activated acid may be a compound that can be isolated, such as an acid chloride, an acid anhydride, a mixed acid anhydride and the like, or may be formed in situ, for example by treatment of an acid with dicyclohexyl carbodiimide (DCC), carbonyl di-imidazole, and the like.

Polyphenol oligomer glycosides may be prepared by the methods described in Toshima, K.,; Tatsuta, K. Chem. Rev., 93, 1503-1531 (1993), Igarashi, K. Adv. Carbohydr. Chem. Biochem., 34, 243 (1977) and D. Kahne et al., J. Am. Chem. Soc., 11, 6881 (1989), or by treatment of a monomer using cyclodextrin glucanotransferase (EC 2.4.1.19, CGTase) according to the procedures described by Funayama et al. to produce a monomer glucoside (M. Funayama, H. Arakawa, R. Yamamoto, T. Nishino, T. Shin and S. Murao, Biosci. Biotech. Biochem., 58, (5), 817-821 (1994)).

According to the process of this invention, polyphenol oligomers, comprised of 2 to 18 monomeric units, may be esterified to provide an esterified polyphenol oligomer, wherein the 3-hydroxyl group on at least one monomeric unit of the oligomer is converted to an ester, wherein the ester moiety may be —OC(O)aryl, —OC(O)-substituted aryl, —OC(O)-styryl, —OC(O)-substituted styryl; wherein said substituted aryl or substituted styryl contains at least one substituent selected from the group consisting of halo, hydroxyl, nitro, cyano, amino, thiol, methylenedioxy, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, and $C_3$-$C_8$ cycloalkoxy. Preferably, the ester moiety, —C(O)-substituted aryl and —C(O)-substituted styryl, is derived from an acid selected from the group consisting of caffeic, cinnamic, coumaric, ferulic, gallic, hydroxybenzoic and sinapic acids.

Additionally, polyphenol oligomers, comprised of 2 to 18 monomeric units, may be glycosylated to provide glycosylated polyphenol oligomers, wherein the 3-hydroxyl group on at least one monomeric unit of the oligomer is converted to a glycosyl ether, wherein the glycosyl moiety may be an —O-glycoside or an —O-substituted glycoside, wherein the substituted glycoside is substituted by —C(O)aryl, —C(O)-substituted aryl, —C(O)-styryl, or —C(O)-substituted styryl; wherein said substituted aryl or substituted styryl may contain the substituents selected from the group consisting of halo, hydroxyl, nitro, cyano, amino, thiol, methylenedioxy, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, and $C_3$-$C_8$ cycloalkoxy. Preferably, the glycoside moiety is derived from a sugar selected from the group consisting of glucose, galactose, xylose, rhamnose and arabinose.

Another embodiment provides a process for halogenating the protected polyphenol monomers, functionalized, protected polyphenol monomers, and polyphenol oligomers prepared according to the process of this invention. A halogenated polyphenol monomer having the formula:

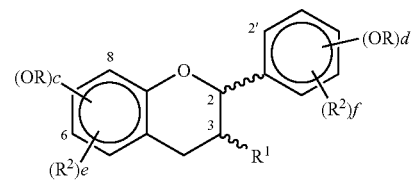

wherein c is 1 to 3; d is 1 to 4; e is 0 to 2; f is 0 to 2, with the proviso that either e or f must be at least 1; R and $R^3$ are independently a protecting group; $R^1$ is H, OH, or $OR^3$; and $R^2$ is halo; may be prepared by the process of treating a polyphenol monomer, wherein e or f are 0, with a halogenating agent for a time and at a temperature sufficient to effect the halogenation of the monomer. The halo group may be chloro, bromo, fluoro, iodo, or mixtures thereof. The bromo group is most preferred. Exemplary halogenating agents that may be useful in this process include N-bromosuccinimide, acetyl hypofluorite, cesium fluoroxysulfate, trifluoromethyl hypofluorite, N-fluoropyridinium salts, 1-chloromethyl-4-fluoro-1,4 diazoniabicyclo[2.2.2]octane bis(tetrafluoroborate), sulfuryl chloride/diphenyl sulfide (in the presence of a Lewis acid), sodium, calcium, or tert-butyl hypochlorite, trimethyl(phenyl) ammonium tetrachloroiodate (III), tetraethylammonium trichloride, iodine/periodic acid, iodine/bis(trifluoroacetoxy)iodobenzene, iodine/copper (II) acetate, iodine/silver sulfate, benzyl trimethylammonium dichloroiodate(I), and the like. Other brominating agents of catechins are described in Ballenegger et al., (Zyma SA) European Patent 0096 007, the disclosure of which is incorporated by reference.

In yet another embodiment of this invention, a halogenated, functionalized polyphenol monomer having the formula:

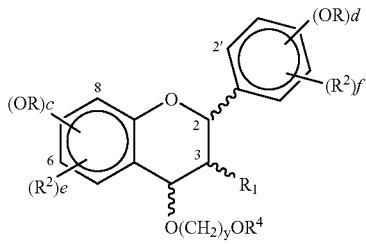

wherein c is 1 to 3; d is 1 to 4; e is 0 to 2; f is 0 to 2; y is 2 to 6; $R^1$ is H, OH, or $R^3$; $R^4$ is H or $R^5$; R, $R^3$, and $R^5$ are independently protecting groups; and $R^2$ is halo; with the proviso that e or f must be 1;

may be prepared by the process of treating a functionalized polyphenol monomer, wherein e and f are 0, with a halogenating agent and for a time and at a temperature sufficient to effect the halogenation of the monomer. The halo group(s) of $R^2$, when e+f are at least 2, may be the same or different, i.e., selected from the group consisting of chloro, fluoro, bromo, and iodo. Advantageously, different halogen substituents may be introduced into the polyphenol monomer. For example, a polyphenol monomer may be subjected to a first halogenation to introduce a halogen substituent, so that for $(R^2)e$, e is 1 and $R_2$ is bromo. This halogenated monomer may then be subjected to a second halogenation to introduce a different halogen substituent, so that for $(R^2)e$, e is 2 and $R_2$ is bromo and fluoro. Similarly, halogenation may be conducted to introduce a different halogen substituents at $(R^2)f$.

Alternatively, one or both of the alkoxy-hydroxyl groups of the functionalized polyphenol monomer may be protected with protecting groups, $R^3$ or $R^5$, prior to halogenation, to provide a monomer having the following formula:

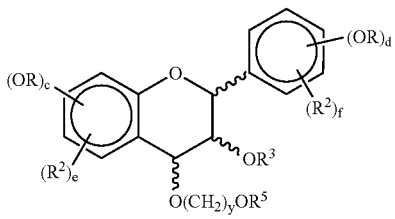

Exemplary alcohol-hydroxyl protecting groups are the same protecting groups (R), described above, that are useful for protecting the phenolic hydroxyl moieties. The protecting group that may be used to protect the alcohol-hydroxyl moieties ($R^3$ or $R^5$) may be the same as or different than the protecting group used to protect the phenolic hydroxyl moieties (R). Preferably, the alcohol-hydroxyl moiety at the 3-position of the polyphenol monomer may be protected using an alkyl silyl protecting group, preferably a tert-butyldimethylsilyl protecting group. Optionally, the alcohol-hydroxyl protecting groups(s) may be removed from the functionalized polyphenol monomer after halogenation or removed after coupling to another monomer or oligomer. Most preferably, the alcohol-hydroxyl protecting group is selected such that removal of the protecting group may be accomplished without removal of the halogen substituent. For example, hydrogenolysis, used to remove benzyl protecting groups, of a benzylated-brominated monomer, will both de-benzylate and de-brominate a monomer or an oligomer. The skilled artisan will recognize that the protecting group(s) and halogen substitutent(s) may be selected such that these groups may advantageously be removed or retained during the protecting, halogenating, coupling, and deprotecting steps.

Limitation of the amount of halogenating agent used during the halogenation reaction will provide for the selective formation of mono-, di-, tri- or tetra-halogenated polyphenol monomers. According to the process of this invention, use of approximately one equivalent of halogenating agent provides for the formation of mono-halogenated monomers, whereas use of 3 equivalents halogenating agent provides for the preparation of tri-bromo protected polyphenol monomers and tri-bromo functionalized protected polyphenol monomers.

The regiochemistry of the halogenation is dependent upon the substitution pattern of the starting polyphenol monomer, specifically, the hydroxyl-substitution pattern of the starting flavanoid monomer. For example, mono-bromination of protected polyphenol monomers, (+)-catechin or (−)-epicatechin, provides for the preparation of the 8-bromo derivatives of these flavanoids. Di-bromination of the protected (+)-catechin or (−)-epicatechin, provides for the preparation of 6,8-dibromo products. Tri-bromination of the protected (+)-catechin or (−)-epicatechin provides for the preparation of 6,8,6'-tribromo products. Accordingly, the process of this invention provides that any and all of the polyphenol monomers or oligomers described therein, may optionally be subjected to halogenation to form novel halogenated polyphenol monomers or oligomers.

A mono-, di-, or tri-halogenated, functionalized, protected polyphenol monomer may be coupled with a protected polyphenol monomer or with a protected polyphenol oligomer to form a novel halogenated, protected polyphenol oligomer using any of the above described procedures. Coupling of the halogenated, functionalized, protected polyphenol monomer with a halogenated, protected polyphenol monomer or with a halogenated, protected polyphenol oligomer forms other novel halogenated polyphenol oligomers. Coupling of the halogenated, functionalized monomer with an 8-halogenated, protected polyphenol monomer or oligomer forms (4α→6) or (4β→6) coupled or branched oligomers. Formation of these branched oligomers may be accomplished only when the protecting groups on the phenolic hydroxyl groups of the halogenated, protected monomer or halogenated, protected oligomer do not prevent reaction due to steric hinderance. For example, when sterically large protecting groups, such as benzyl, are present on the halogenated, protected polyphenol monomer, coupling will not occur, whereas coupling of unprotected polyphenols will provide branched oligomers. Preferably, the halogenated polyphenol oligomers formed herein are brominated polyphenol oligomers. Alternatively, halogenated polyphenol oligomers may also be prepared by direct halogenation of a selected polyphenol oligomer.

A further embodiment of this invention are derivatized or underivatized, halogenated polyphenol monomers having the formula:

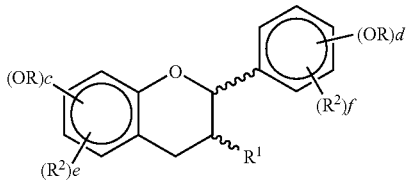

wherein c is 1 to 3; d is 1 to 4; e is 0 to 2; f is 0 to 2; with the proviso that either e or f is at least 1; and,

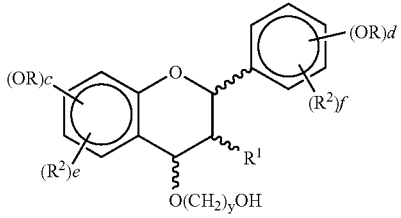

wherein c is 1 to 3; d is 1 to 4; e is 0 to 2; f is 0 to 2; y is 2 to 6; with the proviso that either e or f is at least 1; and, for each of the above, R is a $C_1$-$C_4$ alkyl, benzyl, substituted benzyl, or a silyl moiety containing $C_1$-$C_6$ alkyl or aryl substituents, or, when c or d is 2 and are adjacent, methylene, diphenylmethylene, or substituted diphenylmethylene, wherein said substituted benzyl or each substituted phenyl may contain substituents selected from the group consisting of halo, nitro, cyano, aryl, $C_1$-$C_6$ alkyl, $C_1$-$C_6$ haloalkyl, $C_1$-$C_6$ alkoxy, $C_1$-$C_6$ haloalkoxy, $C_3$-$C_8$ cycloalkyl, $C_3$-$C_8$ cycloalkoxy;

$R^1$ is hydrogen, hydroxy, an —O-glycoside, an —O-substituted glycoside, —OC(O)-aryl, —OC(O)-substituted aryl, —OC(O)-styryl, —OC(O)-substituted styryl; wherein the substituted glycoside is substituted by —C(O)-aryl, —C(O)-substituted aryl, —C(O)-styryl, —C(O)-substituted styrl; and $R^2$ is halo;

wherein said substituted aryl or substituted styryl may contain substituents selected from the group consisting of halo, hydroxyl, nitro, cyano, amino, thiol, methylenedioxy, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, and $C_3$-$C_8$ cycloalkoxy.

Accordingly, yet another embodiment of the invention is directed to a process for preparing a polyphenol oligomer by coupling polyphenol monomers, wherein each phenolic hydroxyl group of the polyphenol monomer is protected, comprising the steps of:

(a) functionalizing the 4-position of a first protected polyphenol monomer to form functionalized polyphenol monomer;

(b) substituting the 6- or 8- position of a protected polyphenol monomer or a protected oligomer to form a blocked, protected polyphenol monomer or oligomer; and (c) coupling the functionalized, protected polyphenol monomer with the blocked, protected polyphenol monomer or oligomer to form the polyphenol oligomer.

Advantageously, the 8-position of the protected polyphenol is blocked such that the 4-position of the functionalized, protected polyphenol monomer is coupled to the 6-position of the blocked, protected polyphenol.

The compounds prepared by the processes of this invention may be purified, e.g., compounds or combinations thereof can be substantially pure; for instance, purified to apparent homogeneity. Purity is a relative concept, and the numerous Examples demonstrate isolation of compounds or combinations thereof, as well as purification thereof, such that by methods exemplified a skilled artisan can obtain a substantially pure compound or combination thereof, or purify them to apparent homogeneity (e.g., purity by HPLC: observation of a single chromatographic peak). As defined herein, a substantially pure compound or combination of compounds is at least about 40% pure, e.g., at least about 50% pure, advantageously at least about 60% pure, e.g., at least about 70% pure, more advantageously at least about 75-80% pure, preferably, at least about 90% pure, more preferably greater than 90% pure, e.g., at least 90-95% pure, or even purer, such as greater than 95% pure, e.g., 95-98% pure.

Moreover, stereoisomers of the oligomers are encompassed within the scope of the invention. The stereochemistry of the substituents on a polyphenol monomeric unit of the oligomer may be described in terms of their relative stereochemistry, "alpha/beta" or "cis/trans", or in terms of absolute stereochemistry, "R/S". The term "alpha" (α) indicates that the substituent is oriented below the plane of the flavan ring, whereas, "beta" (β) indicates that the substituent is oriented above the plane of the ring. The term "cis" indicates that two substituents are oriented on the same face of the ring, whereas "trans" indicates that two substituents are oriented on opposite faces of the ring. The terms R and S are used to denote the arrangement of the substituents about a stereogenic center, based on the ranking of the groups according to the atomic number of the atoms directly attached to that stereogenic center. For example, the flavanoid compound (+)-catechin, may be defined as (2R, trans)-2-(3',4'-dihydroxyphenyl)-3,4-dihydro-2H-1-benzo pyran-3,5,7-triol, or as (2R,3S)-flavan-3,3',4',5,7-pentaol. Interflavan (polyphenol monomeric unit-polyphenol monomeric unit) bonding is often characterized using the relative terms α/β or cis/trans; α/β is used herein to designate the relative stereochemistry of the interflavan bonding.

Linear and branched polyphenol oligomers may be prepared by the process of this invention. Any polyphenol monomer may be used to prepare linear or branched oligomers containing monomeric units having the same or different flavanoid structures. The possible linkages between the monomeric units comprising the oligomers are distinguished by Top (T), Middle (M), Junction (J), and Bottom (B) linkages.

Representative examples for a linear pentamer and branched pentamer are shown below.

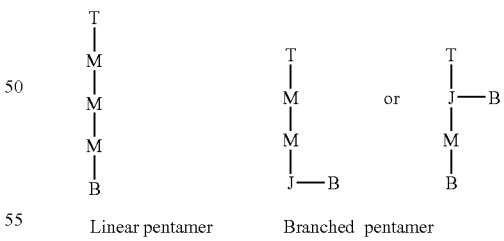

Linear pentamer    Branched pentamer

There are multiple stereochemical linkages, or bonding orientation, between position 4 of a monomeric unit and position 6 and 8 of the adjacent monomeric unit; the stereochemical linkages between monomeric units is designated herein as (4α→6) or (4β→6) or (4α→8) or (4Γ→8) for linear oligomers. In addition to the stereochemical differences in the interflavan bonding to carbon position 4, a bond to carbon position 2 may have alpha or beta stereochemistry, and a bond to carbon position 3 may have alpha or beta stereochemistry (e.g., (−)-epicatechin or (+)-catechin). For linkages to a branched or junction monomeric unit, the stereochemical linkages are (6→4α) or (6→4β) or (8→4α) or (8→4β). When one polyphenol monomeric unit (e.g., C or EC) is linked to another polyphenol monomeric unit (e.g., EC or C), the linkages are advantageously (4α→6) or (4α→8). Further regioisomers of the polyphenol oligomers are encompassed within the scope of this invention. One skilled in the art will appreciate that rotation of a number of bonds within the oligomer may be restricted due to steric hindrance, particularly if the oligomer is substituted, such as with benzyl groups. Accordingly, all possible regioisomers and stereoisomers of the compounds of the invention are encompassed within the scope of the invention.

In yet another embodiment, the invention is directed to a process for the production of a desired regio- or stereoisomer of a polyphenol oligomer of the formula:

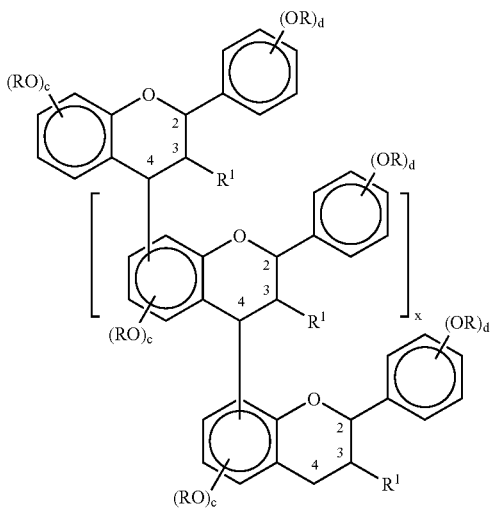

wherein
  x is an integer from 0 to 16;
  c is independently an integer from 1 to 3;
  d is independently an integer from 1 to 4;
  R is independently $C_1$-$C_4$ alkyl, benzyl, substituted benzyl, and a silyl moiety containing $C_1$-$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$-$C_6$ alkyl, $C_1$-$C_6$ haloalkyl, $C_1$-$C_6$ alkoxy $C_1$-$C_6$ haloalkoxy, $C_3$-$C_8$ cycloalkyl, $C_3$-$C_8$ cycloalkoxy; and
  $R^1$ is an —O-glycoside, an —O-substituted glycoside, —OC(O)aryl, —OC(O)-substituted aryl, —OC(O)-styryl, —OC(O)-substituted styryl; wherein the substituted glycoside is substituted by —C(═O)aryl, substituted —C(O)-aryl, —C(O)-styryl, substituted —C(O) styryl; wherein said substituted aryl or substituted styryl may contain the substituents selected from the group consisting of halo, hydroxyl, nitro, cyano, amino, thiol, methylenedioxy, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, and $C_3$-$C_8$ cycloalkoxy; and wherein each phenolic hydroxyl group of a polyphenol monomer is protected, comprising the steps of:
  (a) functionalizing the 4-position of a first polyphenol monomer having a selected stereochemistry;
  (b) coupling said functionalized polyphenol monomer with a second polyphenol monomer having a selected stereochemistry to form a dimer having a selected regiochemistry;
  (c) purifying said dimer;
  (d) if x is equal to 1, functionalizing the 4-position of a third polyphenol monomer having a selected stereochemistry;
  (e) coupling said functionalized third polyphenol monomer having a selected stereochemistry with said dimer to form a trimer having selected regiochemistry;
  (f) purifying said trimer; and
  (g) if x is greater than 1, sequentially adding functionalized polyphenol monomer to said trimer and successively higher oligomers by the steps recited above.

The invention is also directed to a process for producing a polyphenol oligomer of the formula:

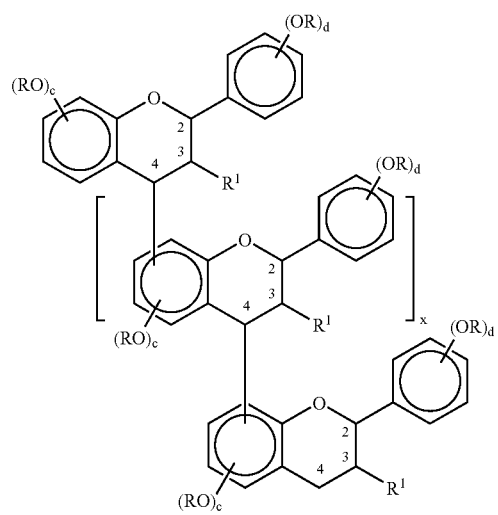

wherein
  a bond to carbon position 2 has alpha or beta stereochemistry;
  a bond to carbon position 3 has alpha or beta stereochemistry;
  a bond to carbon position 4 has alpha or beta stereochemistry;
wherein:
  c is independently an integer from 1 to 3;
  d is independently an integer from 1 to 4;
  x is 0 to 16;
  R is independently $C_1$-$C_4$ alkyl, benzyl, substituted benzyl, and a silyl moiety containing $C_1$-$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$-$C_6$ alkyl, $C_1$-$C_6$ haloalkyl, $C_1$-$C_6$ alkoxy $C_1$-$C_6$ haloalkoxy, $C_3$-$C_8$ cycloalkyl, $C_3$-$C_8$ cycloalkoxy; and
  $R^1$ is hydroxy, an —O-glycoside, an —O-substituted glycoside, —OC(O)-aryl, —OC(O)-substituted aryl, —OC(O)-styryl, or —OC(O)-substituted styryl; wherein the substituted glycoside is substituted by —C(O)-aryl, —C(O)-substituted aryl, —C(O)-styryl, or —C(O)-substituted styryl; wherein said substituted aryl or substituted styryl may contain the substituents selected from the group consisting of halo, hydroxyl, nitro, cyano, amino, thiol, methylenedioxy, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, and $C_3$-$C_8$ cycloalkoxy;

which comprises:
(a) reacting a protected polyphenol monomer of the formula:

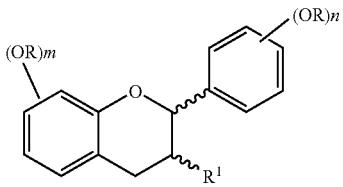

wherein
m is an integer from 1 to 3;
n is an integer from 1 to 4; and
R is a protecting group selected from the group consisting of $C_1$-$C_4$ alkyl, benzyl, substituted benzyl and a silyl moiety containing $C_1$-$C_6$ alkyl or aryl substitutents, or, when c or d is 2 and are adjacent diphenylmethylene and substituted diphenylmethylene a protecting group selected from the group consisting of, wherein said substituted benzyl or each substituted phenyl may contain substitutents selected from the group consisting of halo, nitro, cyano, aryl, $C_1$-$C_6$ alkyl, $C_1$-$C_6$ haloalkyl, $C_1$-$C_6$ alkoxy $C_1$-$C_6$ haloalkoxy, $C_3$-$C_8$ cycloalkyl, $C_3$-$C_8$ cycloalkoxy;
$R^1$ is H or OH;
with a protected phenolic monomer of the formula:

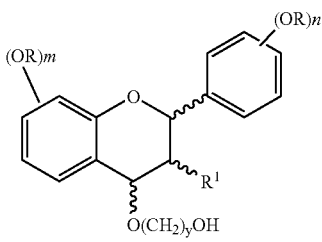

wherein
m is an integer from 1 to 3;
n is an integer from 1 to 4;
y is an integer from 2 to 6;
r is independently a protecting group selected from the group consisting of $C_1$-$C_4$ alkyl benzyl, substituted benzyl, and a silyl moiety containing $C_1$-$C_6$ alkyl or aryl substitutents, or, when c or d is 2 and are adjacent, diphenylmethylene and substituted diphenylmethylene, wherein said substituted benzyl or each substituted phenyl may contain substituents selected from the group consisting of halo, nitro, cyano, aryl, $C_1$-$C_6$ alkyl, $C_1$-$C_6$ haloalkyl, $C_1$-$C_6$ alkoxy $C_1$-$C_6$ haloalkoxy, $C_3$-$C_8$ cycloalkyl, $C_3$-$C_8$ cycloalkoxy; and
R1 is H or OH;
to form a protected polyphenol dimer having protected phenolic hydroxyl groups; and (b) optionally deprotecting the phenolic hydroxyl groups of the protected polyphenol dimer.

In a further embodiment, the invention is directed to a process for the production of a procyanidin polyphenol oligomer, which comprises:
(a) protecting each phenolic hydroxyl group of a (+)-catechin or of a (−)-epicatechin with a protecting group to produce a protected (+)-catechin or a protected (−)-epicatechin;
(b) functionalizing the 4-position of the protected (+)-catechin or of the protected (−)-epicatechin to produce a functionalized protected (+)-catechin or a functionalized protected (−)-epicatechin having the formula:

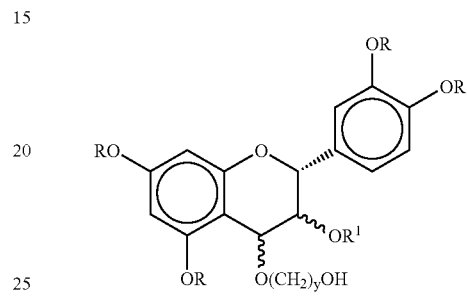

wherein
y is an integer from 2 to 6;
R is a protecting group; and
$R^1$ is hydrogen; and
(c) coupling the protected (+)-catechin or the protected (−)-epicatechin with the functionalized protected (+)-catechin or the functionalized protected (−)-epicatechin to form a protected polyphenol dimer.

In another embodiment, the invention is directed to a process of preparing a procyanidin polyphenol oligomer comprised of n monomeric units of (+)-catechin or (−)-epicatechin, wherein n is an integer from 2 to 18, comprising:
(a) protecting each phenolic hydroxyl group of a (+)-catechin or of a (−)-epicatechin with a suitable protecting group to produce a protected (+)-catechin or a protected (−)epicatechin;
(b) functionalizing the 4-position of the protected (+)-catechin or of the protected (−)-epicatechin to produce a functionalized protected (+)-catechin or a functionalized protected (−)-epicatechin having the formula:

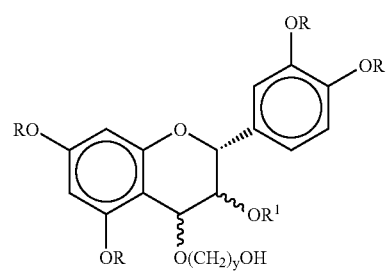

wherein
y is an integer from 2 to 6;
R is a protecting group; and
$R^1$ is hydrogen; and (c) coupling the protected (+)-catechin or the protected (−)-epicatechin with the functionalized protected (+)-catechin or the functionalized protected (−)-epicatechin to produce a protected polyphenol oligomer, wherein n equals 2;

(d) removing the protecting group from each phenolic hydroxyl group of the protected polyphenol oligomer to produce the polyphenol oligomer, wherein n equals 2, (e) coupling the protected polphenol oligomer, wherein n equals 2, with a functionalized protected (+)-catechin or a functionalized protected (−)-epicatechin monomer to produce a protected polyphenol oligomer, wherein n equals 3, (f) removing the protecting group from each phenolic hydroxyl group of the protected polyphenol oligomer to produce the polyphenol oligomer, wherein n equals 3, (g) optionally repeating the process of coupling a protected polyphenol oligomer, where n equals 3 or more, with a functionalized protected (+)-catechin or a functionalized protected (−)-epicatechin monomer to produce protected polyphenol oligomers, wherein n equals 4 to 18, (h) removing the protecting group from each phenolic hydroxyl group of the protected polyphenol oligomer to produce the polyphenol oligomer, wherein n equals 4 to 18.

Advantageously, each phenolic hydroxyl group is protected using a benzyl ether protecting group, and y is 2.

In a further embodiment, the invention is directed to a process for producing a procyanidin polyphenol oligomer of the formula:

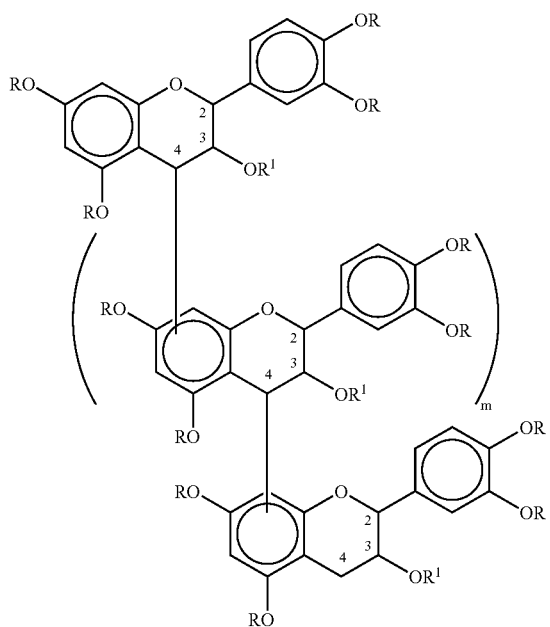

wherein a bond to carbon position 2 has alpha or beta stereochemistry;
a bond to carbon position 3 has alpha or beta stereochemistry;
a bond to carbon position 4 has alpha or beta stereochemistry;

m is 0 to 16;
R is hydrogen; and
$R^1$ is hydrogen; which comprises:

(a) reacting a compound selected from the group consisting of

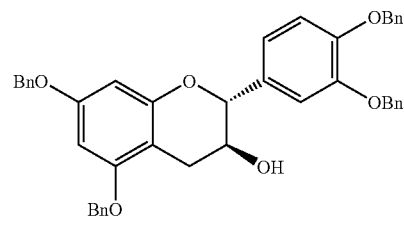

and

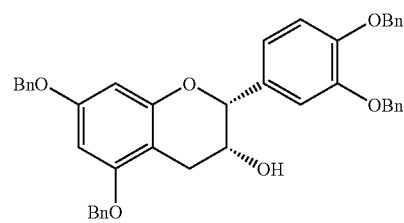

or a mixture thereof, with a compound selected from the group consisting of

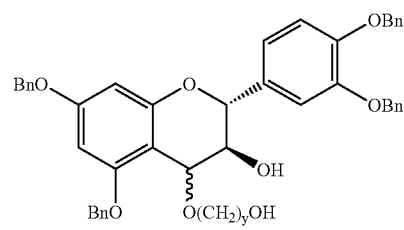

and

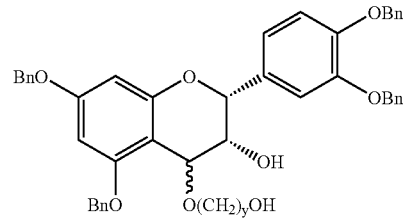

or a mixture thereof,
wherein
y is an integer from 2 to 6; to form a protected polyphenol oligomer having benzylated phenolic hydroxyl groups; and (b) deprotecting the benzylated phenolic hydroxyl groups of the protected polyphenol oligomer.

In a still further embodiment, the invention is directed to a process for producing a polyphenol oligomer of the formula:

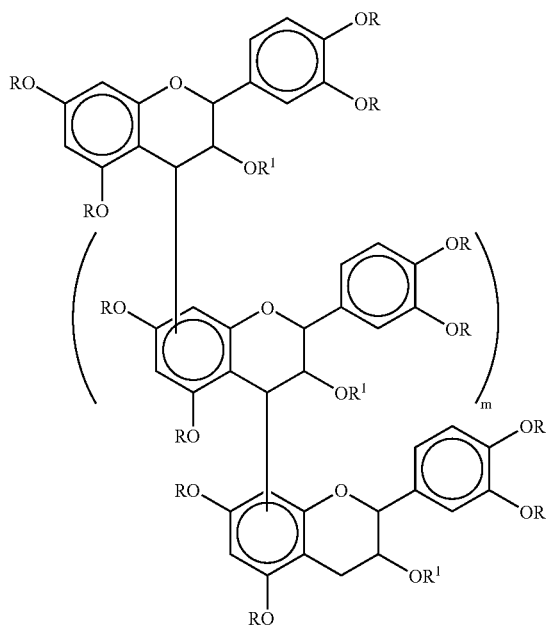

wherein a bond to carbon position 2 has alpha or beta stereochemistry;
a bond to carbon position 3 has alpha or beta stereochemistry;
a bond to carbon position 4 has alpha or beta stereochemistry;
m is 1 to 16;
R is hydrogen; and
$R^1$ is hydrogen;

which comprises:
(a) reacting a compound of the formula:

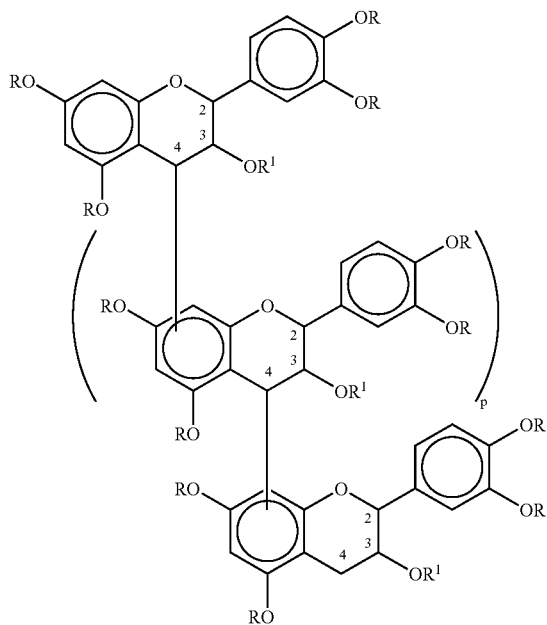

wherein a bond to carbon position 2 has alpha or beta stereochemistry;
a bond to carbon position 3 has alpha or beta stereochemistry;
a bond to carbon position 4 has alpha or beta stereochemistry;
p is 0 to 15;
R is independently $C_1$-$C_4$ alkyl, benzyl, substituted benzyl, and a silyl moiety containing $C_1$-$C_6$ alkyl or aryl substituents, or, when c or d is 2 and are adjacent, diphenylmethylene or substituted diphenylmethylene, wherein said substituted benzyl or each substituted phenyl may contain substituents selected from the group consisting of halo, nitro, cyano, aryl, $C_1$-$C_6$ alkyl, $C_1$-$C_6$ haloalkyl, $C_1$-$C_6$ alkoxy $C_1$-$C_6$ haloalkoxy, $C_3$-$C_8$ cycloalkyl, $C_3$-$C_8$ cycloalkoxy; and
$R_1$ is hydrogen, a glycoside, a substituted glycoside, —C(O)-aryl, —C(O)-substituted aryl, —C(O)-styryl, —C(O)-substituted styryl; wherein the substituted glycoside is substituted by —C(O)aryl, —C(O)-substituted aryl, —C(O)-styryl, —C(O)-substituted styryl; wherein said substituted aryl or substituted styryl may contain the substituents selected from the group consisting of halo, hydroxyl, nitro, cyano, amino, thiol, methylenedioxy, $C_1$-$C_6$ alkyl, $C_1$-$C_6$ alkoxy, $C_1$-$C_6$ haloalkyl, $C_1$-$C_6$ haloalkoxy, $C_3$-$C_8$ cycloalkyl, and $C_3$-$C_8$ cycloalkoxy; with a compound selected from the group consisting of

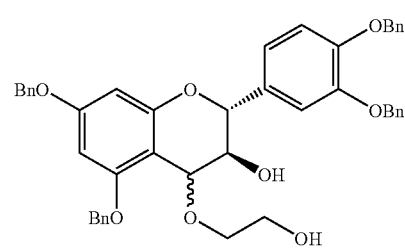

and

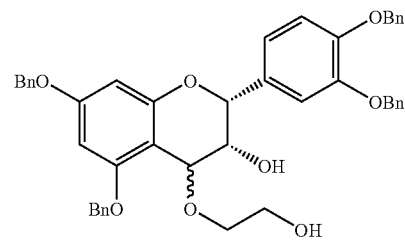

or a mixture thereof,
wherein
m=p+1.

Flavanoid compounds, (+)-catechin and (−)-epicatechin, are used herein to exemplify the types of polyphenol oligomers that may be prepared by the process of this invention. The linkages between the adjacent polyphenol monomeric units, (+)-catechin and (−)-epicatechin, abbreviated C and EC, respectively, are from position 4 to position 6 or position 4 to position 8; and this linkage between position 4 of a monomer and position 6 and 8 of the adjacent monomeric units is designated herein as (4→6) or (4→8).

Examples of compounds within the scope of this invention include dimers, EC-(4β→8)-EC and EC-(4β→6)-EC, wherein EC-(4β→8)-EC is preferred; trimers [EC-(4β→

8)]$_2$-EC, [EC-(4β→8)]$_2$-C and [EC-(4β→6)]$_2$-EC, wherein [EC-(4β→8)]$_2$-EC is preferred; tetramers [EC-(4β→8)]$_3$-EC, [EC-(4β→8)]$_3$-C and [EC-(4β→8)]$_2$-EC(4β→6)-C, wherein [EC-(4β→8)]$_3$-EC is preferred; and pentamers [EC-(4β→8)]$_4$-EC, [EC-(4β→8)]$_3$-EC-(4β→6)-EC, [EC-(4β→8)]$_3$-EC(4β→8)-C and [EC-(4β→8)]$_3$-EC-(4β→6)-C, wherein [EC-(4β→8)]$_4$-EC is preferred. An example of a branched trimer is

examples of a branched tetramer include

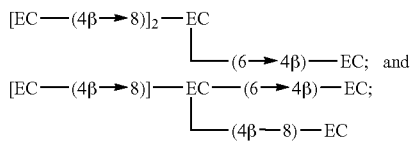

an example of a branched pentamer is

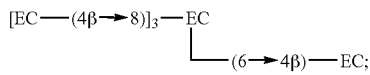

Additionally, compounds which elicit the activities cited above also include hexamers to dodecamers, examples of which are listed below:

A hexamer, wherein one monomer (C or EC) is linked to a pentamer compound listed above, e.g., [EC-(4β→8)]$_5$-EC, [EC(4β→8)]$_4$-EC-(4β→6)-EC, [EC-(4β→8)]$_4$-EC-(4β→8)-C, and [EC-(4β→8)]$_4$-EC-(4β→6)-C; wherein [EC-(4β→8)]$_5$-EC is preferred; an example of a branched hexamer is

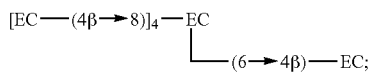

A heptamer, wherein any combination of two monomeric units (C and/or EC) are linked to a pentamer compound listed above, e.g., [EC-(4β→8)]$_6$-EC, [EC-(4β→8)]$_5$-EC-(4β→6)-EC, [EC-(4β→8)]$_5$-EC-(4β→8)-C, and [EC-(4β→8)]$_5$-EC-(4β→6)-C; in a preferred embodiment, the heptamer is [EC-(4β→8)]$_6$-EC; an example of a branched heptamer is

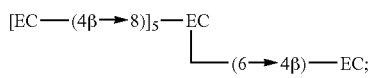

An octamer, wherein any combination of three monomeric units (C and/or EC) are linked to a pentamer compound listed above, e.g., [EC-(4β→8)]$_7$-EC, [EC-(4β→8)]$_6$-EC-(4β→6)-EC, [EC-(4β→8)]$_6$-EC(4β→8)-C, and [EC-(4β→8)]$_6$-EC-(4β→6)-C; in a preferred embodiment, the octamer is [EC-(4β→8)]$_7$-EC; an example of a branched octamer is

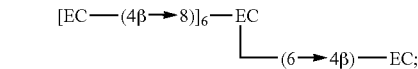

A nonamer, wherein any combination of four monomeric units (C and/or EC) are linked to a pentamer compound listed above, e.g., [EC-(4β→8)]$_8$-EC, [EC-(4β→8)]$_7$-EC-(4β→6)-EC, [EC-(4β→8)]$_7$-EC(4β→8)-C, and [EC-(4β→8)]$_7$-EC-(4β→6)-C; in a preferred embodiment, the nonamer is [EC-(4β→8)]$_8$-EC; an example of a branched nonamer is

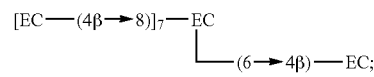

A decamer, wherein any combination of five monomeric units (C and/or EC) are linked to a pentamer compound listed above, e.g., [EC-(4β→8)]$_9$-EC, [EC-(4β→8)]$_8$-EC-(4β→6)-EC, [EC-(4β→8)]8-EC(4β→8)-C, and [EC-(4β→8)]$_8$-EC-(4β→6)-C; in a preferred embodiment, the decamer is [EC-(4β→8)]$_9$-EC; an example of a branched decamer is

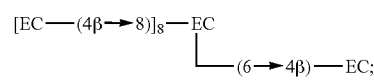

An undecamer, wherein any combination of six monomeric units (C and/or EC) are linked to a pentamer compound listed above, e.g., [EC-(4β→8)]$_{10}$-EC, [EC-(4β→8)]$_9$-EC-(4β→6)-EC, [EC-(4β→8)]$_9$-EC-(4β→8)-C, and [EC-(4β→8)]$_9$-EC-(4β→6)-C; in a preferred embodiment, the undecamer is [EC-(4β→8)]$_{10}$-EC; an example of a branched undecamer is

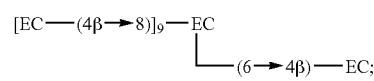

A dodecamer, wherein any combination of seven monomeric units (C and/or EC) are linked to a pentamer compound listed above, e.g., [EC-(4β→8)]$_{11}$-EC, [EC-(4β→8)]$_{10}$-EC-(4β→6)-EC, [EC-(4β→8)]$_{10}$-EC-(4β→8)-C, and [EC-(4β→8)]$_{10}$-EC-(4β→6)-C; in a preferred embodiment, the dodecamer is [EC-(4β→8)]$_{11}$-EC; an example of a branched dodecamer is

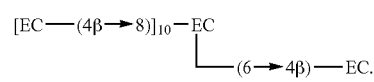

It will be understood from the detailed description that the aforementioned list is exemplary and is provided to illustrate the types of compounds that may be prepared by the processes of this invention and is not intended as an exhaustive list of the compounds encompassed by this invention.

The skilled artisan will recognize that the reaction sequence discussed above may be modified at the final stages to yield oligomers having x=2-16, without undue experimentation. Higher oligomers, i.e., x=2-16, can be isolated by employing the dimer and/or trimer as the starting material for the coupling reaction, and the products derived therefrom may subsequently be used as starting material for coupling reactions to produce even higher oligomers.

Moreover, the skilled artisan will recognize that various reagents may be employed to practice the processes of this invention, without undue experimentation, and without departing from the spirit or scope thereof. Skilled artisans will be able to envision additional routes of synthesis, based on this disclosure and the knowledge in the art, without undue experimentation, e.g, based upon a careful retrosynthetic analysis of the polymeric compounds, as well as the monomers. For example, coupling of polyphenol monomers via an organometallic intermediate has been reported by K. Weinges et al. *Chem. Ber.* 103, 2344-2349 (1970). In addition, linear and branched polyphenol oligomers may be prepared by direct acid catalyzed coupling of monomeric polyphenol units, using conditions described by L. Y. Foo and R. W. Hemingway, *J. Chem. Soc., Chem. Commun.*, 85-86 (1984); J. J. Botha, et al., *J. Chem. Soc.*, Perkin I, 1235-1245 (1981); J. J. Botha et al.; *J. Chem. Soc.*, Perkin I, 527-533 (1982), and H. Kolodziej, *Phytochemistry* 25, 1209-1215 (1986).

Accordingly, yet another embodiment of this invention is directed to a process for preparing a desired regio- or stereoisomer of a polymeric compound of the formula $A_n$, wherein A is a monomer of the formula:

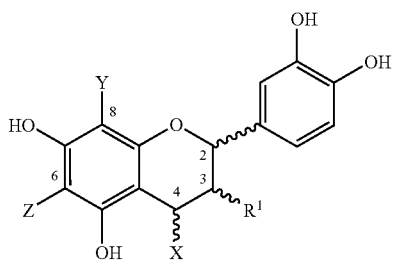

wherein n is 3 to 18, such that there is at least on terminal monomeric unit A, and a plurality of additional monomeric units;

R is 3-($\alpha$)-OH, 3-($\beta$)-OH, 3-($\alpha$)-O-sugar, or 3-($\beta$)-O-sugar;

bonding of adjacent monomers takes place between position 4 and positions 6 or 8;

a bond for an additional monomeric unit in position 4 has $\alpha$ or $\beta$ stereochemistry;

X, Y, and Z are selected from the group consisting of monomeric unit A, hydrogen, and a sugar, with the provisos that as to the at least one terminal monomeric unit, bonding of the additional monomeric unit thereto is at position 4 and optionally Y=Z=hydrogen;

the sugar is optionally substituted with a phenolic moiety, and pharmaceutically acceptable salts, derivatives thereof, and oxidation products thereof;

which process comprises the steps of:
(a) functionalizing the 4-position of a first polyphenol monomer;
(b) reacting the functionalized polyphenol monomer with a second polyphenol monomer to form a dimer;
(c) purifying the dimer;
(d) functionalizing the 4-position of a third polyphenol monomer;
(e) reacting the functionalized third polyphenol monomer with the dimer to form a trimer;
(f) purifying the trimer;
(g) sequentially adding functionalized polyphenol monomer to the trimer and successively higher oligomers by the steps recited above; and
(h) optionally derivatizing the protected or unprotected polyphenol oligomer to form a derivatized polyphenol oligomer.

Preferably, n is 5, the sugar is selected from the group consisting of glucose, galactose, xylose, rhamnose and arabinose, and the phenolic moiety is selected from the group consisting of caffeic, cinnamic, coumaric, ferulic, gallic, hydroxybenzoic and sinapic acids.

The invention is further directed to a process for preparing a polymeric compound of the formula $A_n$, wherein A is a monomer of the formula:

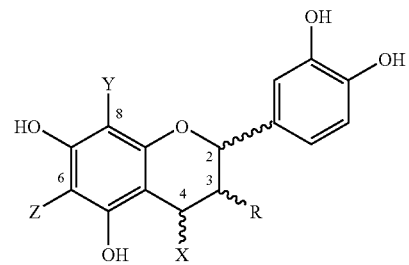

wherein n is 3 to 18, such that there is at least on terminal monomeric unit A, and a plurality of additional monomeric units;

R is 3-($\alpha$)-OH, 3-($\beta$)-OH, 3-($\alpha$)-O-sugar, or 3-($\beta$)-O-sugar;

bonding of adjacent monomers takes place between position 4 and positions 6 or 8;

a bond for an additional monomeric unit in position 4 has $\alpha$ or $\beta$ stereochemistry;

X, Y, and Z are selected from the group consisting of monomeric unit A, hydrogen, and a sugar, with the provisos that as to the at least one terminal monomeric unit, bonding of the additional monomeric unit thereto is at position 4 and optionally Y=Z=hydrogen;

the sugar is optionally substituted with a phenolic moiety, and pharmaceutically acceptable salts, derivatives thereof, and oxidation products thereof;

which process comprises:
(a) protecting each phenolic group of a (+)-catechin or of a (−)-epicatechin with a protecting group to form a protected (+)-catechin or a protected (−)-epicatechin;
(b) functionalizing the 4-position of the protected (+)-catechin or the protected (−)-epicatechin or of the mixture thereof to form a functionalized, protected (+)-catechin, a functionalized protected (−)-epicatechin, or a functionalized protected mixture thereof;
(c) combining the protected (+)-catechin, the protected (−)-epicatechin with the functionalized, protected (+)-catechin, the functionalized, protected (−)-epicatechin, or the mixture thereof to form a protected polyphenol oligomer;
(d) removing the protecting group from the phenolic hydroxyl groups of the polyphenol oligomer to form an unprotected polyphenol oligomer; and (e) optionally derivatizing the protected or unprotected polyphenol oligomer to form a derivatized polyphenol oligomer.

In still another embodiment, the invention is directed to a polymeric compound of the formula An, wherein A is a monomer of the formula:

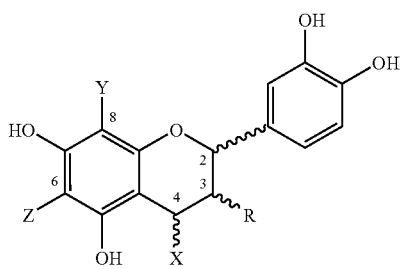

wherein
n is an integer from 3 to 18, such that there is at least one terminal monomeric unit A, and a plurality of additional monomeric units;
R is 3-(α)-OH, 3-(β)-OH, 3-(α)-O-sugar, or 3-(β)-O-sugar;
bonding of adjacent monomers takes place between position 4 and positions 6 or 8;
a bond for an additional monomeric unit in position 4 has alpha or beta stereochemistry;
X, Y and Z are selected from the group consisting of monomeric unit A, hydrogen, and a sugar, with the provisos that as to the at least one terminal monomeric unit, bonding of the additional monomeric unit thereto is at position 4 and optionally Y=Z=hydrogen;
the sugar is optionally substituted with a phenolic moiety, and pharmaceutically acceptable salts, derivatives thereof, and oxidation products thereof.

Preferably, n is 5, the sugar is selected from the group consisting of glucose, galactose, xylose, rhamnose and arabinose, and the phenolic moiety is selected from the group consisting of caffeic, cinnamic, coumaric, ferulic, gallic, hydroxybenzoic and sinapic acids. Also preferably, the compound is substantially pure, preferably purified to apparent homogeneity.

Derivatives of the compound wherein one or more of the phenolic hydroxyl groups is benzylated are also encompassed within the scope of the invention.

Adjacent monomers may bind at position 4 by (4→6) or (4→8); and each of X, Y and Z is H, a sugar or an adjacent monomer, with the provisos that if X and Y are adjacent monomers, Z is H or sugar and if X and Z are adjacent monomers, Y is H or sugar, and that as to at least one of the two terminal monomers, bonding of the adjacent monomer is at position 4 and optionally, Y=Z=hydrogen.

One or more of the monomeric units may be derivatized with a gallate or a β-D-glucose, including the 3-position of a terminal monomeric unit.

These processes may be used to prepare linear or branched oligomers containing repeating monomeric units of a single polyphenol monomer or of different polyphenol monomers. Moreover, given the phenolic character of the subject compounds, the skilled artisan can utilize various methods of phenolic coupling, selective protection/deprotection, organometallic additions, and photochemical reactions, e.g., in a convergent, linear or biomimetic approach, or combinations thereof, together with standard reactions known to those well-versed in the art of synthetic organic chemistry, as additional synthetic methods for preparing polyphenol oligomers. In this regard, reference is made to W. Carruthers, *Some Modern Methods of Organic Synthesis*, 3rd Ed., Cambridge University Press, 1986, and J. March, *Advanced Organic Chemistry*, 3rd Ed., John Wiley & Sons, 1985, van Rensburg et al., *J. Chem. Soc. Chem. Commun.* 24: 2705-2706 (Dec. 21, 1996), Ballenegger et al., (Zyma SA) European Patent 0096 007 B1, all of which are hereby incorporated herein by reference.

The process of this invention also provides a means for incorporation of an isotope label, e.g., deuterium and tritium, into polyphenol oligomers. For example, a polyphenol monomer or oligomer may be dissolved in $D_2O$ and $CD_3CN$, and gently heated in order to initiate H-D exchange (this reaction can also be carried out using $T_2O$ and $CH_3CN$ in order to incorporate a tritium into the molecule). Alternatively, deuterium or tritium may be incorporated using the methods of M. C. Pierre et al., *Tetrahedron Letters* 38, (32), 5639-5642 (1997) or E. Keihlmann et al., *Can. J. Chem.*, 26, 2431-2439 (1988). The incorporation of a deuterium or tritium atom in the polyphenol oligomer facilitates the determination of how polyphenol compounds may be metabolized following ingestion.

The polyphenol oligomers, and derivatives thereof, prepared by the process of this invention have the same uses, and are formulated, purified, and administered in the same manner as described in U.S. patent application Ser. No. 08/831,245 filed Apr. 2, 1997, now U.S. Pat. No. 6,297,273 issued Oct. 21, 2001.

In still yet another embodiment, the invention is directed to a pharmaceutical composition comprising a compound of the formula:

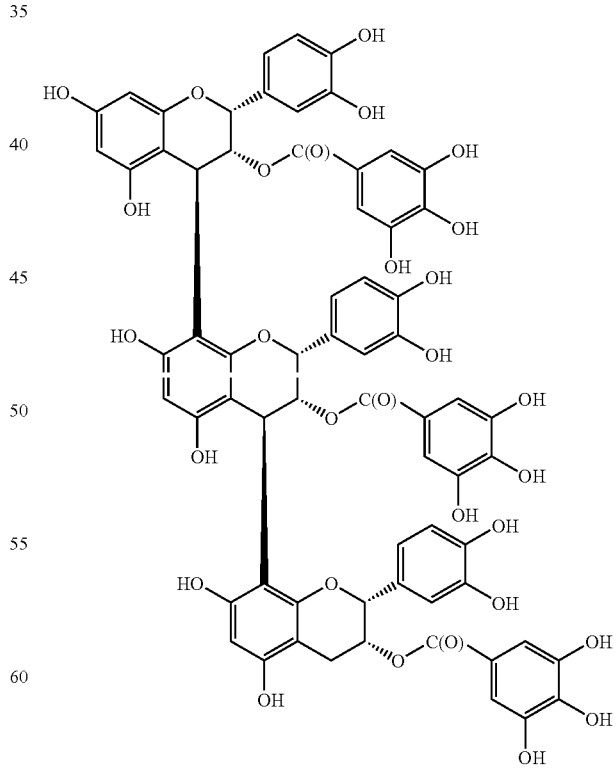

and a pharmaceutically acceptable carrier or excipient, and to a method for treating a subject in need of treatment with an anticancer agent comprising administering to the subject an effective amount of the composition. The cancer includes breast cancer.

Examples 8 and 10 describe the preparation of a dimer bisgallate and a trimer trisgallate, respectively. Their in vitro assessment (Example 25) against several human breast cancer cell lines showed activity equivalent to the pentamer. These results were surprising since gallation of previously inactive procyanidin dimer and trimer substantially increased the antineoplastic activity of these oligomers. Thus, the gallation of oligomers produces compounds that are useful for the uses described in U.S. patent application Ser. No. 08/831,245 filed Apr. 2, 1997, now U.S. Pat. No. 6,297,273 issued Oct. 21, 2001. Further, the following table lists examples of gallated oligomers useful for the uses described in the '273 patent.

Table: Gallated Procyanidin Oligomers
EC-3-O-galloyl-(4β→8)-EC-3-O-gallate
C-3-O-galloyl-(4α→8)-EC-3-O-gallate
C-3-O-galloyl-(4α→8)-C
EC-(4β→8)-EC-3-O-gallate
C-(4α→8)-EC-3-O-gallate
EC-3-O-galloyl-(4β→8)-C
EC (4β→8)-EC-3-O-9-D-glucose-4,6-bisgallate
[EC-3-O-galloyl-(4β→8)]$_2$-EC-3-O-gallate
[EC-3-O-galloyl-(4β→8)]$_3$-EC-3-O-gallate
[EC-(4β→8)]$_4$-EC-3-O-gallate
[EC-(4β→98)]$_5$-EC-3-O-gallate
[EC-(4β→8)]$_6$-EC-3-O-gallate
[EC-(4β→8)]$_7$-EC-3-O-gallate
[EC-(4β→8)]$_8$-EC-3-O-gallate
[EC-(4β→8)]$_9$-EC-3-O-gallate
[EC-(4β→8)]$_{10}$-EC-3-O-gallate
[EC-(4β→8)]$_{11}$-EC-3-O-gallate The Examples which follow are intended as an illustration of certain preferred embodiments of the invention, and no limitation of the invention is implied. The skilled artisan will recognize many variations in these examples to cover a wide range of formulas and processing to rationally adjust the compounds of the invention for a variety of applications without departing from the spirit or scope of the invention.

In the following examples, (+)-catechin and (−)-epicatechin are exemplary polyphenol monomers used to demonstrate the processes of the present invention and no limitation of the invention is implied. The (−)-epicatechin as used herein, may be obtained from commercial sources, or protected epicatechin may be prepared from protected (+)-catechin (Example 3).

EXAMPLE 1

Preparation of (2R,3S, trans)-5,7,3',4'-Tetra-O-benzylcatechin

A solution of (+)-catechin (65.8 g, 226.7 mmol, anhydrous), dissolved in anhydrous dimethylformamide (DMF, 720 mL), was added dropwise, at room temperature over a period of 80 min, to a stirred suspension of sodium hydride, 60% in oil, (39 g, 975 mmol, 4.3 eq.) in DMF (180 mL). (S. Miura, et al., *Radioisotopes,* 32, 225-230 (1983)) After stirring for 50 min, the flask was placed in a −10° C. NaCl/ice bath. Benzyl bromide (121 mL, 1.02 mol, 4.5 eq.) was added dropwise within 80 min. and the brown reaction mixture warmed to room temperature, with stirring, overnight. The resulting reaction mixture was evaporated and the resulting candy-like solid was dissolved, with heating and stirring, in two portions of solvent each consisting of 200 mL of chloroform (CHCl$_3$) and 100 mL of water. The phases were separated, the aqueous phase extracted with CHCl$_3$ (20 mL), and the combined organic phases washed with water (100 mL), dried over magnesium sulfate (MgSO$_4$) and evaporated. The residue was purified by chromatography on silica gel (42×10 cm; ethyl acetate/chloroform/hexane 1:12:7) to provide, after evaporation and drying in vacuo, 85 g crude product, which was recrystallized from trichloroethylene (1.3 L) to provide 35.1 g (24%) of an off-white powder. $^1$H NMR (CDCl$_3$) δ 7.47-7.25 (m, 20H), 7.03 (s, 1H), 6.95 (s, 2H), 6.27, 6.21 (ABq, 2H, J=2 Hz), 5.18 (s, 2H), 5.17 (narrow ABq, 2H), 5.03 (s, 2H), 4.99 (s, 2H), 4.63 (d, 1H, J=8.5 Hz), 4.00 (m, 1H), 3.11, 2.65 (ABq, 2H, J=16.5 Hz, both parts d with J=5.5 and 9 Hz, resp.), 1.59 (d, 1H, J=3.5 Hz); IR (film) 3440 (br), 1618, 1593, 1513, 1499, 1144, 1116, 733, 696 cm$^{-1}$; MS m/z 650 (M+, 0.5%), 319, 181, 91.

Alternatively, the tetra-O-benzyl (+)-catechin may be prepared using the method described by H. Kawamoto et al, *Mokazai Gakkaishi,* 37, (5) 488-493 (1991), using potassium carbonate and benzyl bromide in DMF. Partial racemization of catechin, at both the 2- and 3-positions, was observed by M.-C. Pierre et al., *Tetrahedron Letters,* 38, (32) 5639-5642 (1997).

EXAMPLE 2

Preparation of (2R)-5,7,3',4'Tetrakis(benzyloxy) flavan-3-one

Freshly prepared Dess-Martin periodinane (39.0 g, 92 mmol, prepared by the method of D. B. Dess and J. C. Martin, *J. Am. Chem. Soc.* 113, 7277-7287 (1991) and R. E. Ireland and L. Liu, *J. Org. Chem.* 58, 2899 (1993)), was added at room temperature, all at once, to a stirred solution of the tetra-O-benzylcatechin according to Example 1 (54.4 g, 83.8 mmol) in methylene chloride (420 mL). Within 1.5 h, approx. 30 mL of water-saturated methylene chloride was added dropwise to the reaction mixture to form a turbid amber-colored solution. (S. D. Meyer and S. L. Schreiber, *J. Org. Chem.,* 59, 7549-7552 (1994)) Twenty minutes thereafter, the reaction mixture was diluted with a saturated solution of sodium carbonate (NaHCO$_3$, 500 mL) and a 10% aqueous solution of Na$_2$S$_2$O$_3$.5H$_2$O (200 mL). The phases were separated and the aqueous phase extracted with 50 mL of methylene chloride. The combined organic phases were filtered over silica gel (24×9 cm, chloroform/ethyl acetate 9:1). The eluate was evaporated and dried in vacuo to obtain 50.1 g (92%) of the ketone, which was purified by recrystallization from chloroform/ether: mp 144-144.5° C.; [α]$_D$+ 38.5°, [α]$_{556}$+48.7° (chloroform, c 20.8 g/L); $^1$H NMR (CDCl$_3$) δ 7.45-7.26 (m, 20H), 6.96 (s, 1H), 6.88, 6,86 (ABq, 2H, J=8 Hz, B part d with J=1.5 Hz), 6.35 (narrow ABq, 2H), 5.24 (s, 1H), 5.14 (s, 2H), 5.10 (narrow ABq, 2H), 5.02 (s, 2H), 5.01 (s, 2H), 3.61, 3.45 (ABq, 2H, J=21.5 Hz).

EXAMPLE 3

Preparation of 5,7,3',4'-Tetra-O-benzylepicatechin

A 1 M solution of lithium tri-sec-butylborohydride in tetrahydrofuran, herein after THF, (100 mL, L-Selectride®, sold by the Aldrich Chemical Co, Inc., Milwaukee, Wis.) was added, under an argon atmosphere, to a stirred, 0° C. solution of anhydrous lithium bromide, LiBr, (34.9 g, 402 mmol) in 100 mL anhydrous THF. The resulting mixture was cooled to −78° C., using an acetone/CO$_2$ bath, followed by dropwise addition of a solution of the flavanone according to Example 2 (50.1 g, 77.2 mmol) in 400 mL of anhydrous THF, over a period of 50 min. Stirring was continued at −78° C. for 135 min. The cooling bath was removed and 360 mL of 2.5 M aqueous sodium hydroxide (NaOH) was added to the reaction mixture. The reaction flask was placed in a room temperature water bath and a mixture of 35% aqueous $H_2O_2$ (90 mL) and ethanol (270 mL) was added over a period of 130 min. Stirring was continued overnight. Chloroform (700 mL) was added to dissolve the crystallized product, the phases were separated, the aqueous phase was extracted with $CHCl_3$ (50 mL), the combined organic phases were dried over $MgSO_4$, evaporated and dried in vacuo to provide 56.6 g of crude product. This material was dissolved in 600 mL of a boiling mixture of ethyl acetate (EtOAc) and ethanol (EtOH), (2:3), and allowed to crystallize at room temperature, then in the refrigerator. The product was isolated by suction filtration, washed with 2×50 mL of cold (−20° C.) EtOAc/EtOH (1:3), and dried in vacuo first at room temperature, then at 80° C. to obtain 35.4 g (70%) of a light yellow solid. The evaporated mother liquor was filtered over silica gel, $SiO_2$, (14×6.5 cm, $CHCl_3$, then $CHCl_3$/EtOAc 12:1), the eluate concentrated to 40 mL, and the residue diluted with 60 mL of ethanol, to obtain an additional 5.5 g (11%) of the O-benzylepicatechin as a yellowish solid: mp 129.5-130° C. (from EtOAc/EtOH); $[\alpha]_D$−27.7°, $[\alpha]_{546}$−33.4° (EtOAc, c 21.6 g/L); $^1$H NMR ($CDCl_3$) δ 7.48-7.25 (m, 20H), 7.14 (s, 1H), 7.00, 6.97 (ABq, 2H, J=8.5 Hz, A part d with J=1.5 Hz), 6.27 (s, 2H), 5.19 (s, 2H), 5.18 (s, 2H), 5.02 (s, 2H), 5.01 (s, 2H), 4.91 (s, 1H), 4.21 (br s, 1H), 3.00, 2.92 (ABq, 2H, J=17.5 Hz, both parts d with J=1.5 and 4 Hz, resp.), 1.66 (d, I H, J=5.5 Hz); Anal. Calcd. for $C_{43}H_{38}O_6$: C, 79.36; H, 5.89. Found: C, 79.12: H, 5.99.

EXAMPLE 4

Preparation of (2R,3S,4S)-5,7,3',4'-Tetra O-benzyl-4-(2-hydroxyethoxy)epicatechin Ethylene glycol (6.4 mL, 115 mmol, 5.8 eq.) was added, at room temperature, with stirring, to a solution of the tetra-O-benzylepicatechin according to Example 3 (12.75 g, 19.6 mmol) in 130 mL of anhydrous methylene chloride, followed by addition of 2,3-dichloro-5,6-dicyano-1,4-benzoquinone (DDQ, 8.9 g, 39.2-mmol, 2.0 eq.), at one time, with vigorous stirring. (J.A. Steenkamp, et al., *Tetrahedron Letters*, 26, (25) 3045-3048 (1985)). After approximately 2 hours, 4-dimethylaminopyridine (DMAP, 4.8 g, 39.2 mmol) was added to the reaction mixture, resulting in the formation of a dark green precipitate. After stirring for an additional 5 minutes, 100 g of silica gel was added, and the mixture was concentrated under reduced pressure. The residue was placed on top of a silica gel column (11×6.5 cm) which was eluted with EtOAc/hexane (1:1), and the eluate was concentrated under reduced pressure. The resulting crude material was re-purified by chromatography on silica gel (39×10 cm, EtOAc/hexane (1:2), followed by EtOAc/hexane (2:3)) to provide, after evaporation and drying, in vacuo, 7.3 g (52%) of the benzyl-4-(2-hydroxyethoxy) epicatechin, as a foam or solid, which was recrystallized from acetonitrile: mp 120-121° C.; 1H NMR ($CDCl_3$) δ 7.48-7.26 (m, 20H), 7.14 (d, J=1.5 Hz), 7.02, 6.97 (ABq, 2H, J=8 Hz, A part d with J=1.5 Hz), 6.29, 6.26 (ABq, 2H, J=2 Hz), 5.19 (s, 2H), 5.17 (s, 2H), 5.10 (s, 1H), 5.08, 5.02 (ABq, 2H, partially concealed), 5.00 (s, 2H), 4.59 (d, 1H, J=2.5 Hz), 3.95 (br, 1H), 3.82-3.74 (m, 1H), 3.72-3.57 (m, 3H), 2.17 (br, 1H), 1.64 (d, 1H, J=5.5 Hz); IR (film) 3450 (br), 1616, 1592, 1512, 1152, 11 14, 735, 697 $cm^{-1}$. Anal. Calcd. for $C_{45}H_{42}O_8$: C, 76.04; H, 5.96. Found: C, 76.57; H, 6.02.

EXAMPLE 5

Preparation of O-Benzylepicatechin (4β→8) Oligomers

To a cold (0° C.), stirred solution of the benzyl-4-(2-hydroxyethoxy) epicatechin according to Example 4 (3.28 g, 4.6 mmol) and the tetra-O-benzyl-epicatechin according to Example 3 (12.0 g, 18.4 mmol, 4 eq.) in anhydrous THF (40 mL) and anhydrous methylene chloride (50 mL), was added dropwise, in 10 min, titanium tetrachloride (4.6 mL of 1 M $TiCl_4$ in methylene chloride). (H. Kawamoto et al, *Mokazai Gakkaishi*, 37, (5) 488-493 (1991)) The resulting amber-colored solution was stirred in the ice bath for 5 min, then at room temperature for 90 min. The reaction was terminated by addition of 30 mL of saturated aqueous $NaHCO_3$ and 100 mL of water (resulting pH: 8). The resulting mixture was extracted with methylene chloride (2×20 mL). The combined organic layers were washed with 50 mL of water, dried over $MgSO_4$, evaporated and dried in vacuo. The resulting glass deposited a pink solid upon dissolution in methylene chloride ($CH_2Cl_2$) and standing at room temperature. The solid was filtered off, washed with 3×15 mL of $CH_2Cl_2$/hexane (1:1), and dried in vacuo to obtain 6.1 g of recovered tetra-O-benzylepicatechin. From the evaporated mother liquor, the oligomers were isolated by column chromatography on silica gel (45×5.2 cm). Elution with $CH_2Cl_2$/hexane/EtOAc (13:13:1) provided an additional 4.9 g of recovered tetra-O-benzylepicatechin, followed by 2.17 g of crude O-benzyl dimer. Elution of the dimer was completed using methylene chloride/hexane/EtOAc (10:10:1). Elution of 0.98 g of crude O-benzyl trimer and 0.59 g of higher oligomers was obtained using methylene chloride/hexane/EtOAc (8:8:1 to 6:6:1). The dimer and the trimer were further purified by preparative HPLC on a silica gel column, using ethyl acetate/hexane or ethyl acetate/isooctane as eluent. Peak detection was performed with a UV detector at 265 or 280 nm. Trimer: MS (MALDI-TOF, DHBA matrix) m/z (M+H$^+$) 1949.4; calcd. for $C_{129}H_{110}O_{18}$: 1947.8; (M+Na$^+$) 1971.2; calcd. for $C_{129}H_{110}O_{18}Na$: 1969.8; (M+K$^+$) 1988.3; calcd. for $C_{129}H_{110}O_{18}K$: 1985.7.

EXAMPLE 6

Preparation of Epicatechin Dimer

To a solution of the O-benzyl-dimer according to Example 5 (22.3 mg, 17.2 μmol) in 0.5 mL of ethyl acetate was added sequentially, 2 mL of methanol and 7.2 mg of 10% Pd/C. The mixture was stirred under 1 bar of $H_2$ for 3 hours and filtered over cotton. The filtration residue was washed with methanol and the combined filtrates were evaporated. An NMR spectrum of the crude product indicated the presence of benzylated material. The procedure was therefore repeated, with the amount of catalyst increased to 17.5 mg and the time extended to 3.7 h. The crude polyphenol dimer (9.6 mg) was purified by preparative HPLC ($C_{18}$ reverse phase column water/methanol (85:15) with addition of 0.5% acetic acid, detection at 265 nm) to provide 4.5 mg (45%) of polyphenol dimer as an amorphous film. $^1$H NMR (300 MHz, acetone-$d_6$/$D_2O$ 3:1 (v/v), TMS) δ 7.19 (br, 1H), 7.01 (overlapping s+br, 2H), 6.86-6.65 (m, 4 H), 6.03 (br, 3H), 5.10 (br, 1H), 5.00 (br, 1H), 4.69 (br, 1H), 3.97 (s, 1H), 2.92, 2.76 (br ABq, 2H, J=17

Hz); MS (MALDI-TOF, DHBA matrix) m/z (M+K$^+$) 616.8; calcd. for $C_{30}H_{26}O_{12}K$: 617.1; (M+Na$^+$) 600.8; calcd. for $C_{30}H_{26}O_{12}Na$: 601.1.

EXAMPLE 7

Preparation of O-Benzylepicatechin Dimer Bisgallate

To a solution of tri-O-benzyl gallic acid (38 mg, 87 µmol, 5 eq.), DMF (1 µL) in methylene chloride (0.6 mL), was added oxalyl chloride (15 µL, 172 µmol, 10 eq.). The resulting reaction mixture was stirred at room temperature for approximately 1 hour, evaporated and dried in vacuo to provide tri-O-benzyl galloyl chloride. A solution of the O-benzyl-dimer according to Example 5 (22.5 mg, 17.3 µmol) in anhydrous pyridine (0.5 mL) was added to the crude galloyl chloride at room temperature, and the resulting mixture was stirred for 44.5 h. After addition of 20 µL of water, stirring was continued for 2.5 h, followed by addition of 10 mL of 5% HCl. The resulting mixture was extracted with methylene chloride (3×5 mL), the combined organic phases were dried over $MgSO_4$, evaporated and purified by filtration over silica gel using with $EtOAc/CHCl_3$ (1:19). Concentration of the eluate and drying in vacuo yielded 36.0 mg (97%) of the O-benzyl dimer bisgallate as a colorless film: $[\alpha]_D$–53-3°, $[\alpha]_{546}$–65.60 ($CH_2Cl_2$, c 15.7 g/L); IR (film) 1720, 1591, 1498, 1428, 1196, 1112, 736, 696 cm$^{-1}$; MS (MALDI-TOF, DHBA matrix) m/z (M+K$^+$) 2181.8; calcd. for $C_{142}H_{118}O_{20}K$: 2181.8; (M+Na$^+$) 2165.9; calcd. for $C_{142}H_{118}O_{20}Na$: 2165.8.

EXAMPLE 8

Preparation of Epicatechin Dimer Bisgallate

To a solution of the O-benzyl dimer bisgallate according to Example 7 (33.8 mg, 15.8 µmol) in 4 mL of THF was added sequentially 4 mL of methanol, 0.2 mL of water, and 42 mg of 20% $Pd(OH)_2/C$. The mixture was stirred under 1 bar of $H_2$ for 75 minutes and filtered over cotton. The filtration residue was washed with 2.2 mL of methanol/$H_2O$ (10:1) and the combined filtrate was concentrated under reduced pressure to provide 14.2 mg of yellowish, amorphous crude product. A 7.2 mg aliquot was purified by preparative HPLC (silica gel, ethyl acetate/hexane; detection at 280 nm) to yield 5.0 mg (71%) of the polyphenol dimer bisgallate as a turbid pinkish glass from which small amounts of ethanol and acetic acid could not be removed: $^1$H NMR (acetone-d$_6$/D$_2$O 3:1 v/v, TMS, most signals broad) δ 7.08 (s, 2H, sharp), 7.1-6.7 (m, 7H), 6.66 (d, 1H, sharp, J=8 Hz), 6.17 (s, 1H), 5.94 (s, 2H), 5.70 (s, 1H), 5.49 (s, 1 H), 5.44 (s, 1H), 4.9 (very br, 1H), 4.80 (s, 1H), 3.08, 2.88 (ABq, 2H, J=17 Hz, A part d, J=4 Hz); MS (MALDI-TOF, DHBA matrix) m/z (M+Na$^+$) 904.9; calcd. for $C_{44}H_{34}O_{20}Na$: 905.2.

EXAMPLE 9

Preparation of O-Benzylepicatechin Trimer Trisgallate

Using the procedure described in Example 7, O-benzyl trimer trisgallate was obtained from the O-benzyl trimer according to Example 5 in 78%. yield after purification by HPLC (conditions: silica gel, ethyl acetate/hexane, 280 nm); 1H NMR: extremely complex; IR (film) 3031, 1719, 1594, 1498, 1428, 1116, 735, 696 cm$^{-1}$.

EXAMPLE 10

Preparation of Epicatechin Trimer Trisgallate

Using the procedure described in Example 8, polyphenol trimer trisgallate was obtained from the O-benzyl trimer trisgallate according to Example 9 in 60% yield after purification by HPLC. ($C_{18}$ reverse phase gradient of 15-25% B in A, where A is 0.5 vol. % acetic acid (AcOH) in water and B is 0.5% AcOH in ethanol; 280 nm); $^1$H NMR (300 MHz, $D_2O$/acetone-d$_6$ 1:3 (v/v)) δ 7.10 (s, 2H), 7.1-6.88 (m, 7H), 6.82-6.70 (m, 3H), 6.68-6.60.

EXAMPLE 11

Preparation of 8-Bromo-5,7,3',4'-tetra-O-benzylepicatechin

Method A: To a solution of 116 mg (178 µmol) of tetra-O-benzylepicatechin in 4 mL of anhydrous $CH_2Cl_2$ was added with ice cooling and stirring 32 mg (180 µmol) of N-bromosuccinimide (NBS). Stirring at 0° C. was continued for 100 min, the solution was concentrated, and the residue was purified by chromatography on silica gel (15× 1.8 cm) with $CHCl_3/EtOAc$ (25:1). Crystallization from $CHCl_3$/ethanol gave 110 mg (85%) of a colorless, cotton-like solid. Mp 137.5° C.; $[\alpha]_D$–50.4°, $[\alpha]_{546}$–60.7° (c 17.3 g/L, EtOAc); $^1$H NMR (300 MHz, CDCl$_3$, TMS) δ 7.5-7.25 (m, 20H), 7.23 (d, 1H, J=1.5 Hz), 7.03, 6.98 (ABq, 2H, J=8.5 Hz, A part d with J=1 Hz), 6.25 (s, 1H), 5.22 (s, 2H), 5.19 (s, 2H), 5.11 (s, 2H), 5.02, 4.96 (ABq, 2H, J=9 Hz), 4.98 (s, 1H), 4.27 (br s, 1H), 3.04, 2.90 (ABq, 2H, J=17.5 Hz, both parts d with J=1.5 and 4 Hz, resp.), 1.58 (d, 1H, J=4.5 Hz); $^{13}$C NMR (75 MHz, CDCl$_3$) δ 156.86, 154.79, 151.65, 149.09, 148.73, 137.31, 137.15, 136.77, 136.72, 130.82, 128.67, 128.65, 128.58, 128.56, 128.09, 127.98, 127.87, 127.50, 127.31, 127.25, 127.13, 118.91, 115.17, 113.07, 102.85, 93.07, 78.62, 71.35, 71.20, 70.31, 65.92, 28.00; IR (mineral oil suspension) 3571, 1606, 1581, 1518, 1184, 1129, 771, 732, 694 cm$^{-1}$; MS m/z 399/397 (1/1%), 332 (1%0), 181 (8%), 91 (100%). Anal. calcd. for $C_{43}H_{37}O_6Br$: C, 70.78; H, 5.11. Found: C, 70.47; H, 5.10.

Method B: To 563 mg (771 µmol) of 5,7,3',4-tetra-8-bromocatechin, prepared by the method described in Example 1, in 5 mL of $CH_2CL_2$ was added at room temperature all at once 425 mg (1.00 mmol) of Dess-Martin periodinane. Water-saturated $CH_2Cl_2$ was added dropwise within 40 min to produce a slight turbidity. After another 20 min, 20 mL each of saturated $NaHCO_3$ solution and a 10% aqueous solution of $Na_2S_2O_3.5H_2O$ were added. The phases were separated and the aqueous phase extracted with 3×15 mL of ether. The combined organic phases were concentrated and the residue filtered over silica gel (20×2.5 cm, ether/hexane 1:1). The eluate was evaporated and dried in vacuo to obtain 522 mg (93%) of the ketone as a colorless foam: $^1$H NMR (CDCl$_3$ δ 7.47-7.25 (m, 20H), 7.04 (d, 1H, J=1 Hz), 6.85, 6.81 (ABq, 2H, J=8.5 Hz, B part d with=8.5 Hz), 3.52, 3.48 (ABq, 2H, J=21.5 Hz); $^{13}$C NMR (CDCl$_3$ δ 203.99, 155.55, 155.40, 150.68, 148.98, 137.06, 136.90, 136.28, 136.04, 128.64, 128.62, 128.46, 128.41, 128.22, 128.05, 127.78, 127.76, 127.35, 127.17, 127.13, 127.08, 126.99, 118.86, 114.59, 112.43, 103.54, 93.96, 93.87, 82.91, 71.25, 71.04, 70.98, 70.38, 33.30; IR (film) 1734, 1605, 1513, 1099, 737 696 cm$^{-1}$.

To 598 mg (822 µmol) of the above crude ketone in 8.2 mL of anhydrous THF was added dropwise within 10 min 1.23 mL of a 1 M solution of lithium tri-sec-butylborohydride (L-Selectride®). After stirring at −78° C. for 3h, starting material was still detectable in the reaction mixture by thin layer chromatography, "TLC," (SiO$_2$, EtOAc/hexane 1:3), and another 1.23 mL of the reducing agent was added. Stirring was continued for another 4 h while the temperature was gradually allowed to rise to −4° C. Aqueous NaOH (2.5 M, 6 mL) and 4 mL of 35% aqueous H$_2$O$_2$ were added with continued cooling; the resulting exotherm raised the bath temperature to +12° C. Stirring in the water bath was continued overnight, then the mixture was partially evaporated, and 20 mL ether and 10 mL of EtOAc were added. The phases were separated, and the aqueous phase was extracted with 50 mL of EtOAc. The combined organic phases evaporated, and the residue was purified by chromatography on silica gel (23×2.5 cm) with EtOAc/hexane 1:3 to obtain 327 mg (55%) of the product as a light-yellow foam.

EXAMPLE 12

Preparation of O-Methylepicatechin Tetramer

The O-methylepicatechin trimer (prepared according to Examples 1 through 5, except that in Example 1, methyl iodide or dimethyl sulfate and potassium carbonate in acetone is used to prepare the protected monomer, tetra-O-methylcatechin) is brominated in position 8 of the top epicatechin moiety using either of the procedures of Example 11. The resulting bromo derivative is reacted with 5,7,3',4'-tetra-O-methyl-4-(2-hydroxyethoxy)epicatechin according to Example 5 to yield a mixture of tetramers having the fourth epicatechin moiety attached to the 6-positions predominantly of the bottom and center epicatechin moieties, as well as higher oligomers. The desired intermediate,

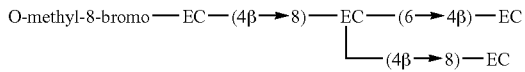

is isolated by preparative HPLC as in Example 11. The purified intermediate is de-brominated by treatment of its THF solution at low temperature, preferably at −78° C., with an excess of an alkyllithium, preferably n- or tert-butyllithium, and protonation of the resulting solution or suspension of the lithiated protected branched tetramer by addition of a weak proton acid, such as water or an alcohol.

EXAMPLE 13

Preparation of O-Benzylepicatechin Tetramer Tetragallate

Using the procedure described in Example 7, the O-benzylepicatechin tetramer tetragallate is obtained from the O-benzylepicatechin tetramer according to Example 12.

EXAMPLE 14

Preparation of Epicatechin Tetramer Tetragallate

Using the procedure described in Example 8, the epicatechin tetramer tetragallate is obtained from the O-benzylepicatechin tetramer tetragallate according to Example 13.

EXAMPLE 15

3,5,7,3',4-Penta-O-benzyl-8-bromoepicatechin

To 53 mg (1.3 mmol) of sodium hydride (60% suspension in mineral oil) was added with stirring at 0° C. under N$_2$ 738 mg (1.01 mmol) of 5,7,3',4-tetra-O-benzyl-8-bromoepicatechin in 2 mL of anhydrous DMF. After 10 min, 0.18 mL (1.5 mmol) of neat benzyl bromide was added. The mixture was stirred at 0° C. for 145 min and at room temperature for 5.5 h, then 0.1 mL of water was added. Chromatography on SiO$_2$ (27×2.6 cm) with EtOAc/hexane 1:4 and drying in vacuo (room temperature, then 80° C.) yielded 650 mg (78%) of the product as a yellowish glass: $[\alpha]_D$−52.6°, $[\alpha]_{546}$−63.40 (EtOAc, c 17.9 gL$^{-1}$); $^1$H NMR (CDCl$_3$) δ 7.50-7.14 (m, 23H), 6.99 (m, 2H), 6.94, 6.91 (ABq, 2H, J=8.5 Hz, A part d with J=1.5 Hz), 6.23 (s, 1H), 5.19 (s, 2H), 5.11 (s, 5H), 4.97 (S, 2H), 4.38, 4.30 (ABq, 2H, J=12.5 Hz), 3.97 (narrow m, 1H), 2.95, 2.80 (ABq, 2H, J=17 Hz, both parts d with J=3.5 and 4.5 Hz, resp.); $^{13}$C NMR (CDCl$_3$) δ 156.44, 154.62, 151.94, 148.65, 137.92, 137.41, 137.26, 136.75, 136.71, 131.68, 128.56, 128.53, 128.38, 128.12, 128.00, 127.85, 127.70, 127.62, 127.43, 127.33, 127.25, 127.19, 127.02, 119.15, 114.74, 113.29, 103.40, 93.11, 92.76, 78.06, 72.13, 71.32, 71.26, 71.21, 70.83, 70.22, 24.73; IR (film) 1605, 1580, 1513, 1454, 1346, 1265, 1125, 1095, 735, 697; IR (film) 1605, 1580, 1513, 1454, 1346, 1265, 1125, 1095, 735, 697 cm$^{-1}$. Anal. Calcd. for C$_{50}$H$_{43}$O$_6$Br: C, 73.26; H, 5.29. Found C, 72.81; H, 5.12.

EXAMPLE 16

5,7,3',4-Tetra-O-benzyl-6,8-dibromoepicatechin

To a solution of 334 mg (914 μmol) of 5,7,3',4-tetra-O-benzylepicatechin in 10 mL of anhydrous CH$_2$Cl$_2$ was added with ice cooling all at once 192 mg (1.08 mmol) of recrystallized $^N$-bromosuccinimide (NBS). The reaction mixture was stirred at 0° C. for 45 min and at room temperature for 17 h. A solution of 200 mg of Na$_2$S$_2$O$_3$.5H$_2$O in 5 mL of water was added. After brief stirring, the phases were separated, the aqueous phase was extracted with 5 mL of CH$_2$Cl$_2$, and the combined organic phases were dried over MgSO$_4$ and evaporated. Chromatography on silica gel (30× 2.6 cm) with EtOAc/CHCl$_3$/hexane 1:12:7 (to remove a trace byproduct) then 3:12:7, was followed by evaporation and drying in vacuo to give 362 mg (87%) of the dibromide as a colorless foam: $[\alpha]_{546}$−58.20, (EtOAc, c 13.5 gL$^{-1}$); $^1$H NMR (CDCl$_3$) δ 7.64 (d, 2H, J=7 Hz), 7.52-7.26 (m, 18 H), 7.17 (s, 1H), 7.03, 6.97 (s, 2H), 5.20 (s, 2H), 5.17 (s, 2H), 5.03 (s, 2H), 5.01, 4.97 (ABq, 2H, J=11 Hz), 4.99 (s, 1 h), 4.19 (narrow m, 1H), 3.04, 2.87 (ABq, J=17.5 Hz, both parts d with J=1.5 and 3.5 Hz, resp.), 1.55 (d, 1H, J=3.5 Hz); $^{13}$C NMR (CDCl$_3$) δ 154.43, 152.57, 151.09, 149.03, 148.82, 137.10, 136.94, 136.50, 136.37, 130.13, 128.52, 128.50, 128.48, 128.47, 128.43, 128.35, 128.32, 128.16, 127.82, 127.81, 127.36, 127.20, 118.81, 115.06, 112.91, 112.30, 105.23 103.25, 78.80, 74.61, 74.55, 71.24, 71.14, 65.33, 28.75; IR (film) 1734, 1606, 1513, 1369, 1266, 1184, 1113, 1083, 735, 697 cm$^{-1}$. Anal. Calcd, for C$_{43}$H$_{36}$O$_6$Br$_2$: C, 63.88; H, 4.49. Found: C, 64.17; H, 4.45.

EXAMPLE 17

5,7,3',4'-Tetra-O-benzyl-6,8,6'-tribromoepicatechin

To a solution of 1.72 g (2.65 mmol) of 5,7,3',4-tetra-O-benzylepicatechin in 26 mL of anhydrous CH$_2$Cl$_2$ was added with ice cooling all at once 1.89 g (10.6 mmol) of recrystallized N-bromosuccinimide. The reaction mixture was stirred at 0° C. for 1 h and at room temperature for 20 h. A solution of 3 g of $Na_2S_2O_3 \cdot 5H_2O$ in 25 mL of water was added. Partial phase separation occurred only after addition of 30 mL of brine, 230 mL of water, and 130 mL of $CH_2Cl_2$. Residual emulsion was set aside, the aqueous phase was extracted with 100 mL of $CH_2Cl_2$, and this organic phase and 200 mL of water were shaken in a separatory funnel with the emulsion. Again phase separation was incomplete, and the remaining emulsion was extracted a last time with 100 mL of $CH_2Cl_2$. The combined organic phases were dried over $MgSO_4$ and concentrated. Chromatography on silica gel (17×4.5 cm) with $EtOAc/CHCl_3$/hexane 1:12:7, then 1:15:4 was followed by evaporation and drying in vacuo to give 2.01 g (85%) of the tribromide as a light-tan solid. The analytical sample was obtained by crystallization from $CHCl_3$/EtOH: mp 154-156° C.; $[\alpha]_D$–112°, $[\alpha]_{546}$–135° (EtOAc, c 9.7 $gL^{-1}$); $^1H$ NMR ($CDCl_3$ δ 7.66 (d, 2H, 6.5 Hz), 7.52 (d, 2H, J=6.5 Hz), 7.48-7.26 (m, 17H), 7.14 (s, 1H), 5.28 (s, 1H), 5.23 (s, 2H), 5.17 (s, 2H), 5.06 (s, 2H), 5.02 (s, 2H), 4.44 (narrow m, 1H), 3.10, 2.95 (ABq, J=17 Hz, A part br, B part d with J=4 Hz), 1.35 (d, 1H, J=4 Hz); $^{13}C$ NMR ($CDCl_3$ δ 154.54, 152.53, 151.09, 149.15, 148.32, 136,49, 136.44, 136.40, 136.31, 128.72, 128.54, 128.52, 128.48, 128.42, 128.36, 128.33, 128.16, 128.02, 127.89, 127.41, 127.27, 118.84, 114.58, 112.30, 111.42, 105.38, 103.14, 78.61, 74.62, 74.58, 71.46, 70.96, 62.66, 28.99; IR (film) 1499, 1385, 1367, 1266, 1182, 1109, 1083, 734, 695 $cm^{-1}$. Anal. Calcd. for $C_{43}H_{35}O_6Br_3$: C, 58.20; H, 3.98. Found: C, 58.52; H, 3.80.

EXAMPLE 18

(2R,3S,4S)-5,7,3',4'-Tetra-O-benzyl-8-bromo-4-(2-hydroxyethoxy)epicatechin

Method A: To a solution of 202 mg (284 μmol) of (2R,3S,4S)-5,7,3',4'-tetra-O-benzyl-4-(2-hydroxyethoxy) epicatechin in 4 mL of $CH_2Cl_2$ was added at –78° C. all at once 51 mg (286 μmol) of recrystallized N-bromosuccinimide. The reaction mixture was stirred in the thawing cold bath, which after 65 min had reached 0° C. A solution of 50 mg of $Na_2S_2O_3 \cdot 5H_2O$ in 1 mL of water was added, the cold bath was removed, and the mixture was stirred for 15 min at room temperature. The phases were separated, and the organic phase was extracted with 5 mL of $CH_2Cl_2$. The combined organic phases were dried over $MgSO_4$, concentrated, and purified via chromatography on silica gel (33×1.6 cm) with EtOAc/hexane 1:1 (Note 1). After starting material and mixed fractions containing comparable concentrations of both components had been eluted, fractions consisting mostly of the desired product were collected. These fractions were further purified by preparative HPLC (Whatman Partisil 10,500×9.4 mm, EtOAc/hexane 1:1, 5 mL/min, detection at 280 nm). The major peak with $t_R$ 14.4 min was isolated: $^1H$ NMR ($CDCl_3$) δ 7.49-7.25 (m, 20 H), 7.23 (d, 1H, J=1 Hz), 7.05, 6.98 (ABq, 2H, J=8 Hz, A part d with J=1.5 Hz), 6.28 (s, 1H), 5.23 (s, 3H), 5.19 (s, 2H), 5.12 (s, 2H), 5.05, 4.99 (ABq, 2H, J=11.5 Hz), 4.63 (d, 1H, J=3 Hz), 4.03 (br, 1H), 3.83-3.76 (m, 1H), 3.74-3.56 (m, 3H), 2.11 (br, 1H), 1.57 (br, 1H); $^{13}C$ NMR ($CDCl_3$) δ 158.30, 156.61, 152.17, 149.09, 148.73, 137.18, 137.07, 136.39, 136.02, 130.04, 128.68, 128.61, 128.49, 128.46, 128.33, 127.98, 127.79, .127.60, 127.45, 127.23, 126.93, 118.95, 115.16, 113.24, 103.36, 92.78, 75.05, 71.30, 71.21, 71.09, 70.83, 70.70, 70.23, 67.90, 61.89; IR (film). 3380 (br), 1603, 1577, 1514, 1187, 1130, 1111, 733, 696 $cm^{-1}$.

Method B: To 44.1 mg (43.3 μmol) of the bis(TBDMS) ether of Example 19, dissolved in 0.4 mL of anhydrous THF, was added 0.19 mL of a tetrabutylammonium fluoride solution (1 M in THF). The mixture was stirred in a closed flask for 4 hours, then evaporated, and the residue was purified via chromatography on silica gel (15×1.8 cm) with $EtOAc/CHCl_3$/hexane 1:12:7 (to remove a forerun), then 1:19:0. The eluate was evaporated and dried in vacuo to yield 32.7 mg (96%) of the product as a colorless film.

EXAMPLE 19

(2R,3S,4S)-5,7,3',4'-Tetra-O-benzyl-3-O-(tert-butyldimethylsilyl)-4-[2-[(tert-butyldimethylsilyl)oxy]ethoxy]epicatechin To solution of 2.18 g (3.07 mmol) of (2R,3S,4S)-5,7,3'-4'-tetra-O-benzyl-4-(2-hydroxyethoxy)epicatechin and 0.63 g (9.2 mmol) of imidazole in 5 mL of anhydrous DMF was added at room temperature, all at once, 1.30 g (8.6 mmol, 2.8 eg.) of tert-butyldimethylsilyl chloride. The mixture was stirred at room temperature in a stoppered flask for 24 h and then directly filtered over silica gel (33×3.7 cm) with EtOAc/hexane 1:6 to give, after evaporation and drying in vacuo, 2.63 g (91) of the product as a colorless glass: $[\alpha]_D$+3.9°, $[\alpha]_{546}$+4.70 (EtOAc, c 9.0 $gL^{-1}$); $^1H$ NMR ($CDCl_3$) δ 7.51-7.28 (m, 20H), 7.12 (d, 1H, J=1 Hz), 6.98, 6.93 (ABq, 2H, J=8 Hz, A part d with J=1 Hz), 6.24, 6.22 (ABq, 2H, J=2 Hz), 5.19, 5.14 (ABq, 2H, partially concealed), 5.17 (s, 2H), 5.09-4.96 (2 overlapping ABq, 4H), 4.50 (d, 1H, J=3 Hz), 3.89 (br d, 1H, J=2.5 Hz), 3.69 (m, 4H), 0.88 (s, 9H), 0.67 (s, 9H), 0.04 (s, 3H), 0.03 (s, 3H), –0.21 (s, 3H), –0.48 (s, 3H); $^{13}C$ NMR ($CDCl_3$) δ 160.12, 159.39, 156.63, 148.88, 148.30, 137.37, 137.02, 136.83, 132.65, 128.53, 128.49, 128.42, 128.38, 127.94, 127.82, 127.75. 127.67, 127.62, 127.51, 127.33, 127.26, 120,14, 115.28, 114.29, 102.23, 94.28, 93.17, 75.22, 71.5, 71.40, 70.63, 70.32, 70.11, 69.98, 69.61, 62.71, 25.95, 25.59, 18.38, 17.90, –5.10, –5,18, –5.25, –5.40; IR (film) 2952, 2928, 2855, 1616, 1593, 1257, 1153, 1136, 1108, 835, 777, 735, 696 cm⁻. Anal. Calcd, for $C_{57}H_{70}O_8Si_2$: C, 72.88; H, 7.51. Found: C, 73.35; H, 7.04.

EXAMPLE 20

(2R,3S,4S)-5,7,3',4'-Tetra-O-benzyl-8-bromo-3-O-(tert-butyldimethylsilyl)-4-[2-[tert-butyldimethylsilyl)oxy]ethoxy]epicatechin To a solution of 2.61 g (2.78 mmol) of (2R,3S,4S) –5,7,3',4'-tetra-O-benzyl-3-O-(tert-butyldimethylsilyl)-4-[2-[(tert-butyldimethylsilyl)oxy]ethoxy]epicatechin, in 35 mL of $CH_2Cl_2$ was added at –78° C., all at once, 500 mg (2.81 mmol) of recrystallized N-bromosuccinimide. The reaction mixture was stirred in the thawing cold bath, which after 6 h had reached +20° C. A solution of 0.5 g of $Na_2S_2O_3 \cdot 5H_2O$ in 10 mL of water was added, the cold bath was removed, and the mixture was stirred for 10 min at room temperature. The phases were separated, and the organic phase was extracted with 5 mL of $CH_2Cl_2$. The combined organic phases were concentrated and filtered over silica gel with EtOAc/hexane 1:4. Evaporation and drying in vacuo resulted in 2.72 g (96%) of the product as a colorless glass: $[\alpha]_D$–25.8°, $[\alpha]_{546}$–31.6° (EtOAc, c 20.2 $gL^{-1}$); $^1H$ NMR ($CDCl_3$) δ 7.51-7.25 (m, 20H), 7.22 (s, 1H), 6.98, 6.94

(ABq, 2H, J=8 Hz, A part br), 6.22 (s, 1H), 5.30 (s, 1 H), 5.19 (s, 2H), 5.17 (s, 2H), 5.11 (s, 2H), 5.06, 4.98 (ABq, 2H, J=12 Hz), 4.54 (d, 1H, J=3 Hz), 3.94 (br d, 1H, J=2.5 Hz), 3.73-3.60 (m, 4H), 0.88 (s, 9H), 0.60 (s, 9H), 0.04 (s, 3H), 0.03 (s, 3H), −0.24 (s, 3H), −0.56 (s, 3H); $^{13}$C NMR (CDCl$_3$) δ 158.04, 156.11, 152,88, 148,92, 148.05, 137.42, 137.31, 136.62, 136.59, 132.24, 128.59, 128.52, 128.41, 128.37, 128.01, 127.85, 127.69, 127.63, 127.45, 127.31, 127.19, 126.99, 119.46, 115.41, 113.76, 103.75, 92.61, 91.79, 75.78, 71.60, 71.05, 71.03, 70.61, 70.47, 70.14, 69.30, 62.65, 25.94, 25.47, 18.39, 17.90, −5,10, −5.19, −5.50; IR (film) 2952, 2928, 285, 1605, 1578, 1257, 1186, 1135, 1114, 835, 777, 735, 696 cm$^{-1}$. Anal. Calcd. for $C_{57}H_{69}O_8BrSi_2$: C, 67.24; H, 6.83. Found: C, 67.35; H, 6.57.

EXAMPLE 21

(2R,3S,4S)-5,7,3',4'-Tetra-O-benzyl-6,8,6'-tribromo-3-O-(tert-butyldimethylsilyl)-4-[2-[(tert-butyldimethylsilyl)oxy]ethoxy]epicatechin To a solution of 96.0 mg (94.3 μmol) of (2R,3S,4S)-5,7,3',4'-tetra-O-benzyl-8-bromo-3-O-(tert-butyldimethylsilyl)-4-[2-[(tert-butyldimethylsilyl)oxy]ethoxy]epicatechin in 1.2 mL of CH$_2$Cl$_2$ was added at room temperature, all at once (65 mg, 365 μmol, 3.87 eq.) of recrystallized N-bromosuccinimide. The reaction mixture was held at room temperature for 20.5 h, then a solution of 0.5 g of Na$_2$S$_2$O$_3$.5H$_2$O in 5 mL of water was added, and the mixture was stirred for 10 min at room temperature. The phases were separated, and the organic phase was extracted with 2×5 mL of CH$_2$Cl$_2$. The combined organic phases were concentrated and filtered over silica gel (34×1.1 cm) with EtOAc/hexane 1:12. Evaporation and drying in vacuo resulted in 90.3 mg (81%) of the product as a colorless glass $[α]_{546}$−74.1° (EtOAc, c 9.0 gL$^{-1}$); $^1$H NMR (CDCl$_3$) δ 7.64 (d, 2H, J=7Hz), 7.60 (d, 2H, J=7 Hz), 7.49-7.28 (m, 17H), 7.13 (s, 1H), 5.62 (s, 1H), 5.24, 4.97 (ABq, 2H. J=11 Hz), 5.16 (s, 4 H), 5.09 (s, 2H), 4.53, 4.43 (ABq, 2H. J=2.5 Hz, B past br), 3.09-3 81 (m, 1H), 3.80-3.71 (m, 3H), 0.84 (s, 9H), 0.65 (s, 9H), −0.02 (s, 3H), −0.16 (s, 3 H), −0.57 (s, 3H) (one Si—CH$_3$ signal presumably coinciding with TMS); $^{13}$C NMR (CDCl$_3$) δ 156.15, 154.11, 153.92, ]48.72, 148.65, 136.90, 136.69, 136.58, 136.38, 129.61, 128.52, 128.50, 128.45, 128.43, 128.32, 128.16, 127.94, 127.91, 127.64, 127.44, 127.33, 119.23, 115.83, 113.33, 110.94, 104.76, 103.01, 75.85, 75.64, 74.56, 71.75, 71.50, 70.89, 70.79, 64.27, 62.55, 25.97, 25.58, 18.44, 17.73, −5.24, −5.30, −5.80; IR (film) 2927, 2856, 1499, 1360, 1259, 1106, 836 cm$^-$.

EXAMPLE 22

(2R,3S,4S)-5,7,3'4'-Tetra-O-benzyl-6,8,6'-tribromo-4-(2-hydroxyethoxy)epicatechin To 73.4 mg (62.4 μmol) of the bis(TBDMS) ether in 0.4 mL of anhydrous THF was added 0.25 mL of tetrabutylammonium fluoride solution (1 M in THF). The mixture was stirred in a closed flask for 2.5 h, then evaporated, and the residue was purified via chromatography on silica gel (15×1 cm) with EtOAc/hexane 1:2 (to remove a forerun), then 1:1. The evaporated eluate was further purified by preparative thin layer chromatography (SiO$_2$, 200×200×2 mm, EtOAc/hexane 1:1) to yield 44.8 mg (76%) of the product as a colorless film: $[α]_D$−81.6°, $[α]_{546}$−98.3° (EtOAc, c 10.1 gL$^{-1}$); $^1$H NMR (CDCl$_3$) δ 7.65 (d, 2H. J=6.5 Hz), 7.54 (d, 2H. J=6.5 Hz), 7.48-7.24 (m, 17H), 7.13 (s, 1H), 5.57 (s, 1H), 5.24, 5.08 (ABq, 2H. J=11 Hz), 5.22, 5.18 (A3q, 2H. J=11.5 Hz), 5.13 (s, 2H), 5.06 (s, 2H), 4.45 (d, 1H, J=HZ), 4.25 (br, 1 H), 3.84-3.76 (m, 1H), 3.72-3.58 (m, 3H), 2.11 (br, 1 H), 1.48 (br, 1H); $^{13}$C NMR (CDCl$_3$) 156.24, 154.70, 151.52, 149.24, 148.39, 136.50, 136.38, 136.18, 128.60, 128.58, 128.52, 128.51, 128.49, 128.44, 128.09, 128.06, 128.03, 127.94, 127.46, 127.27, 118.92, 115.03, 112.99, 111.33, 105.40. 103.41, 76.04, 75.08, 74.66, 71.50, 71.08, 71.03, 70.96, 64.12, 61.95; IR (film) 3500 (br), 1580, 1500. 1365, 1262, 1193. 1121, 1097, 736, 696 cm$^{-1}$.

EXAMPLE 23

[5,7,3,4'-Tetra-O-benzyl-8-bromo-3-O-(tert-butyldimethylsilyl)epicatechin]-(4,8)-(5,7,3',4'-tetra-O-benzylepicatechin)

To a solution of 97.3 mg (95.6 μmol) of (2R,3S,4S)-5,7,3',4'-tetra-O-benzyl-8-bromo-3-O-(tert-butyldimethylsilyl)-4-[2-[(tert-butyldimethylsilyl)oxy]ethoxy]epicatechin and 311 mg (478 μmol, 5 eq.) of 5,7,3',4'-tetra-O-benzylepicatechin in 0.85 mL of anhydrous THF and 1.1 mL of anhydrous CH$_2$Cl$_2$ was added with stirring and exclusion of moisture at 0° C., 0.10 mL (0.10 mmol) of a 1 M solution of TiCl$_4$ in CH$_2$Cl$_2$. After 140 min at room temperature, 5 mL of saturated aq. NaHCO$_3$ and 10 mL of CH$_2$Cl$_2$ were added, the phases were separated, and the aqueous phase was extracted with 2×10 mL of CH$_2$Cl$_2$. The combined organic phases were dried over MgSO$_4$ and evaporated, and the residue was filtered over silica gel with EtoAc/toluene 1:19. Evaporation and drying in vacuo gave 239 mg of a foam the components of which could be separated only by preparative HPLC (Whatman Partisil 10, 500×9.4 mm, EtOAc/toluene 1:24, 5 mL/min, detection at 290 nm). From 234 mg of this mixture, 34.8 mg of the desired product was obtained at $t_R$ 10.3 min. Remaining minor impurities were removed by additional preparative HPLC (Whatman Partisil 10,500×9.4 mm, EtOAc/hexane 1:4, 5 mL/min, detection at 280 nm, $t_R$ 16.1 min) to yield 30.3 mg (21%) of the title compound as a glass: $[α]_D$+16.2°, $[α]_{546}$+19.40 (EtOAc, c 12.3 gL$^{-1}$); $^1$H NMR (CDCl$_3$) (two rotamers) δ 7.5-6.7 (m), 6.26 (s), 6.22 (s), 6.14 (s), 6.09 (s), 5.99 (s), 5.52 (s), 5.44 (s), 5.20-4.71 (m), 4.56, 4.37 (ABq, J=12.5 Hz), 4.12 (br), 3.90 (br s), 3.74 (br), 3.03, 2.95 (ABq, minor rotamer, J=17 Hz., both parts d with J=2.5 and 3.5 Hz, resp.), 2.92, 2.81 (ABq, major rotamer, J=18 Hz, B part d win J=4.5 Hz), 1.35 (s), 0.54 (s), 0.50 (s), −0.31 (s), −0.54 (s); IR (film) 2927, 1603, 1512, 1267, 1111, 734, 696 cm$^{-1}$; MS (ES) m/z 1512.8, 1511.9, 1510.8, 1509.8, 1508.8 (M+NH$_4^+$; calcd. for $^{13}C^{12}C_{91}H_{91}^{81}BrNO_{12}Si/^{12}C_{92}H_{91}^{81}BrNO_{12}Si/$ $^{13}C^{12}C_{91}H_{91}^{79}BrNO_{12}Si/^{12}C_{92}H_{91}^{79}BrNO_{12}Si$: 1511.5/1510.5/1509.5/1508.5).

EXAMPLE 24

(5,7,3',4'-Tetra-O-benzyl-8-bromoepicatechin)-(4,8)-(5,7,3',4'-tetra-O-benzylepicatechin)

Method A: To a solution of 78.6 mg (99.5 μmol) of (2R,3S,4S)-5,7,3',4'-tetra-O-benzyl-8-bromo-4-(2-hydroxyethoxy)epicatechin and 324 mg (498 μmol, 5 eq.) of 5,7,3',4'-tetra-O-benzylepicatechin in 0.85 mL of anhydrous THF and 1.1 mL of anhydrous CH$_2$Cl$_2$ was added with stirring and exclusion of moisture at 0° C. 0.10 mL (0.10 mmol) of a 1 M solution of TiC$_4$ in CH$_2$Cl$_2$. After 3.5 h at room temperature, 3 mL of an saturated NaHCO$_3$ aqueous solution and 10 mL of $CH_2Cl_2$ were added, the phases were separated, and the organic phase was dried over $MgSO_4$ and evaporated. The residue was filtered over $SiO_2$ eluting sequentially with $EtOAc/CHCl_3$/hexane 1:12:7 (to remove most of the unreacted tetra-O-benzylepicatechin), then 1:19:0. The desired product was isolated from the evaporated crude product by preparative HPLC (Whatman Partisil 10,500×9.4 mm, EtOAc/hexane 1:4, 5 mL/min, detection at 280 nm, $t_R$ 27.5 mm) to obtain 36.3 mg (26%) of a glass.

Method B: To a solution of 60.4 mg (46.5 µmol) of O-benzylated epicatechin 4,8-dimer in 0.9 mL of anhydrous $CH_2Cl_2$ was added at −78° C. all at once 8.3 mg (47 µmol) of recrystallized N-bromosuccinimide. The reaction mixture was stirred and allowed to thaw to 0° C. during 1.5 h, then stirred at 0° C. for 40 min. Thin Layer chromatography of the mixture ($SiO_2$, EtOAc/toluene 1:9) showed that some material with the same mobility as the starting material ($R_f$ 0.49) was present besides a product ($R_f$ 0.43). The mixture was re-cooled to −40° C., and an additional 2.2 mg (12 µmol) of NBS was added. After the mixture had thawed to 0° C. within 70 min., the thin layer chromatogram of the mixture remained unchanged, and the reaction was terminated by briefly stirring at room temperature with a solution of 0 1 g of $Na_2S_2O_3 \cdot 5H_2O$ in 2 mL of water. The phases were separated, and the aqueous phase was extracted with 5 mL of $CH_2Cl_2$. Evaporation, filtration over silica gel (10×1.1 cm) with $EtOAc/CH_2Cl_2$/hexane 1:6:3, and again evaporation gave 65 mg of a crude mixture which was separated by preparative TLC ($SiO_2$, 200×200×2 mm, EtOAc/toluene 1:15, 2 developments) and additionally purified by preparative HPLC (Whatman Partisil 10, 500×9.4 nm, EtOAc/hexane 1:4, 5 mL/min, detection at 280 nm). The major product obtained thereby was identical by NMR with the one obtained above: $[\alpha]_D$, $[\alpha]_{546}$+0.6° (EtOAc, c 8.4 $gL^{-1}$); $^1H$ NMR ($CDCl_3$ (two rotamers) δ 7.5-6.8 (m), 6.78 (d, J=8 Hz), 6.74 (d, J=1 Hz), 6.34 (s), 6.27 (dd, J=1, 8 Hz), 6.19 (s), 6.16 (s), 6.02 (s), 5.56 (s), 5.36 (s), 5.2-4.95 (m), 4.9-4.7 (m), 4.60, 4.36 (ABq, J=12 Hz), 4.33 (br), 4.11 (br), 3.99 (s), 3.80 (br), 3.08-2.80 (2 ABq, minor rotamer A part at 3.04, J=17.5 Hz, B part not discernible; major rotamer at 2.96, 2.85, J=18 Hz, B part d with J=4.5 Hz), 1.66 (d, J=5 Hz), 1.58 (d, J=5 Hz), 1.40 (d, J=3.5 Hz), 1.28 (partially overlapping with solvent-derived impurity); IR (film) 1604, 1512, 1266, 1117, 735, 696 $cm^{-1}$; MS (ES) m/z 1398.6, 1397.6, 1396.6, 1395.6, 1394.6 ($M+NH_4^+$; calcd. for $^{13}C^{12}C_{85}H_{77}^{81}BrNO_{12}/^{12}C_{86}H_{77}^{81}BrNO_{12}/$ $^{13}C^{12}C_{85}H_{77}^{79}BrNO_{12}/^{12}C_{86}H_{77}^{79}BrNO_{12}$: 1397.5/1396.5/1395.5/1394.5).

EXAMPLE 25

Cytotoxic Activity

Figure 1B:
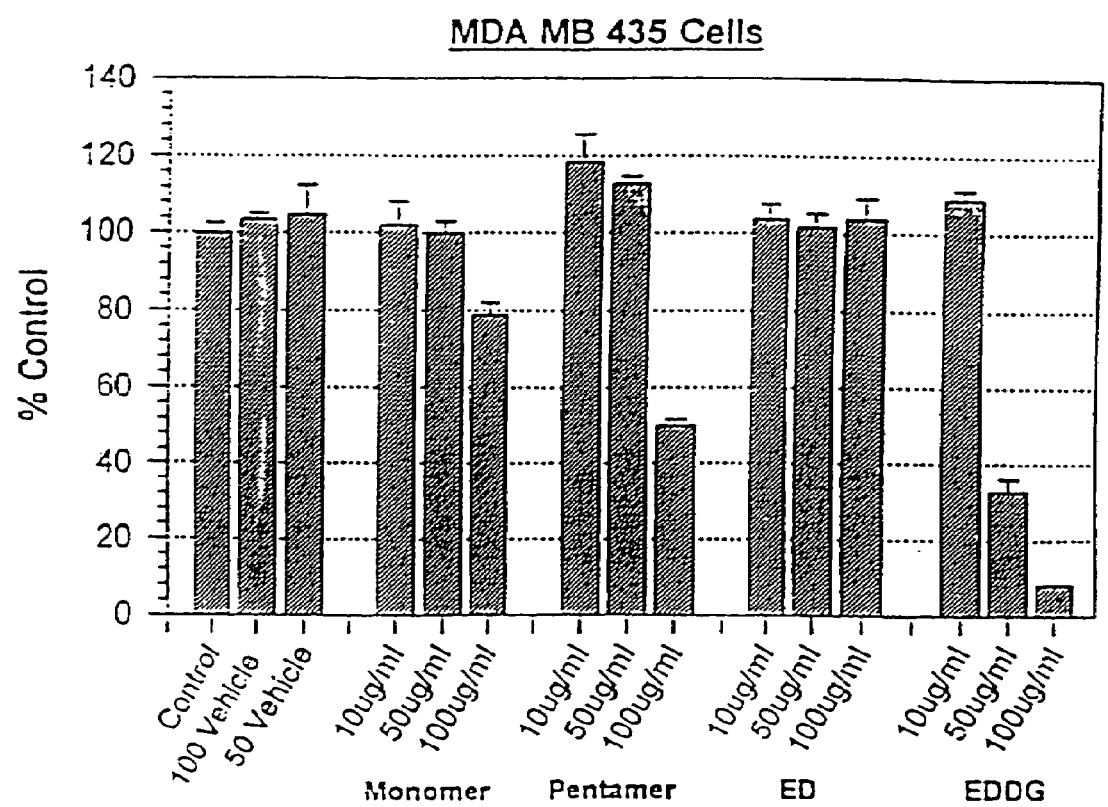
FIG. 1(b) is a bar graph showing the dose-response relationship between the control (solvent vehicle), monomer (epicatechin), pentamer (purified by preparative HPLC), ED (synthetic epicatechin dimer (EC-(4β→8)-EC)), and EDDG (synthesized epicatechin dimer bisgallate (EC-3-O-galloyl-(4β→8)-EC-3-O-gallate)) against the human breast cancer cell line MDA MB 435 at various µg/mL concentrations.
Figure 1C:
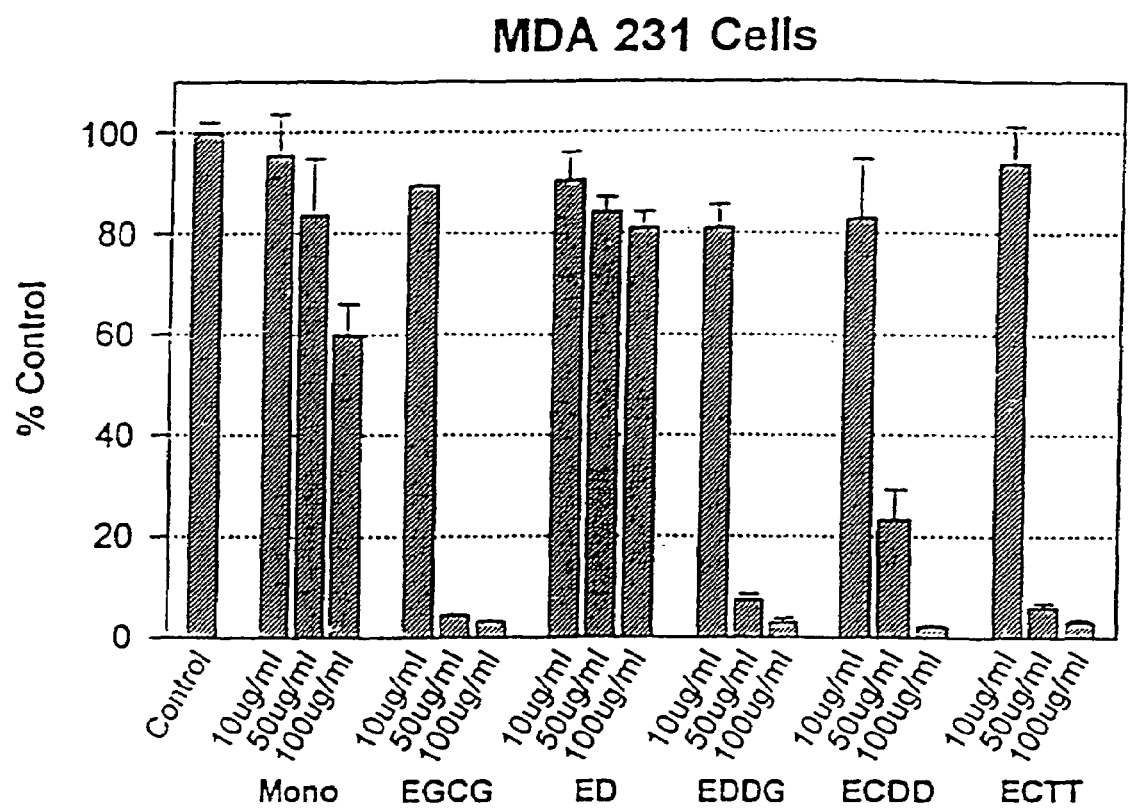
FIG. 1(c) is a bar graph showing the dose-response relationship between the control (solvent vehicle), monomer (epicatechin), EGCG (epigallocatechin gallate from Sigma), ED (synthesized epicatechin dimer (EC-(4β→8)-EC)), EDDG (synthesized epicatechin dimer bisgallate (EC-3-O-galloyl-(4β→8)-EC-3-O-gallate)), ECDD (repeated synthesis of epicatechin dimer bisgallate (EC-3-O-galloyl-(4β→8)-EC-3-O-gallate)), and ECTT (synthesized epicatechin trimer trisgallate ([EC-3-O-galloyl-(4β→8)]₂-EC-3-O-gallate)) against the human breast cancer cell line MDA 231 at various μg/mL concentrations.
Figure 1D:
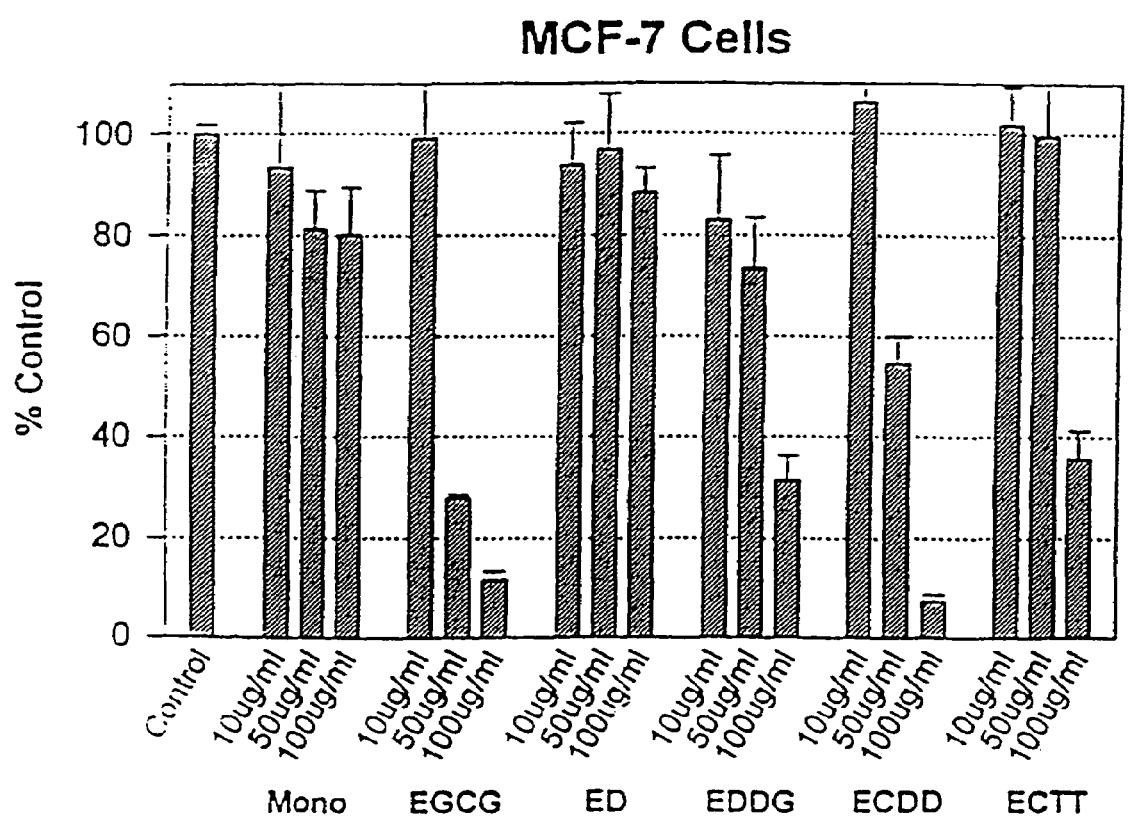
FIG. 1(d) is a bar graph showing the dose-response relationship between the control (solvent vehicle), monomer (epicatechin), EGCG (epigallocatechin gallate from Sigma), ED (synthesized epicatechin dimer (EC-(4β→8)-EC)), EDDG (synthesized epicatechin dimer bisgallate (EC-3-O-galloyl-(4β→8)-EC-3-O-gallate)), ECDD (repeated synthesis of epicatechin dimer bisgallate (EC-3-O-galloyl-(4β→8)-EC-3-O-gallate)), and ECTT (synthesized epicatechin trimer trisgallate ([EC-3-O-galloyl(4β→8)]₂-EC-3-O-gallate)) against the human breast cancer cell line MCF-7 at various μg/mL concentrations.

The epicatechin dimer bisgallate (abbreviated ECDG) and epicatechin trimer trisgallate (abbreviated ECTG) were screened for activity against certain breast cancer cell lines, and the results are presented graphically in FIG. 1(a)-(d).

All human tumor cell lines were obtained from the American Type Culture Collection. Cells were grown as monolayers in IMEM containing 10% fetal bovine serum without antibiotics. The cells were maintained in a humidified, 5% $CO_2$ atmosphere at 37° C.

After trypsinization, the cells were counted and adjusted to a concentration of 1,000-2,000 cells per 100 mL. Cell proliferation was determined by plating the cells (1,000-2,000 cells/well) in a 96 well microtiter plate. After addition of 100µL cells per well, the cells were allowed to attach for 24 hours. At the end of the 24 hour period, various polyphenol derivatives were added at different concentrations to obtain dose response results. The polyphenols were dissolved in media at a 2 fold concentration and 100 µL of each solution was added in triplicate wells. On consecutive days, the plates were stained with 50 µL crystal violet (2.5 g crystal violet dissolved in 125 mL methanol, 375 mL water), for 15 min. The stain was removed and the plate was gently immersed into cold water to remove excess stain. The washings were repeated two more times, and the plates allowed to dry. The remaining stain was solubilized by adding 100 µL of 0.1 M sodium citrate/50% ethanol to each well. After solubilization, the number of cells were quantitated on an ELISA plate reader at 540 nm (reference filter at 410 nm).

Cancer cell line growth at the end of four days was plotted as the percent growth of the control and is shown in FIG. 1(a)-(d) as bar graphs. Error bars represent ± standard deviation of three replicate measurements. The data indicated that the monomer (epicatechin) and synthetic epicatechin dimer showed no cytotoxicity against the breast cancer cell lines investigated. However, the synthetic epicatechin dimer bisgallate and synthetic epicatechin trimer trisgallate elicited a cytotoxic effect equivalent to the pentamer and/or epigallocatechin gallate, especially at higher dosages.

It was surprisingly found that the dimer bisgallate and trimer trisgallate exhibited great antineoplastic activity when compared to the underivatized dimer and trimer. These results indicated that gallation of the previously inactive cocoa procyanidin oligomers substantially increases the antineoplastic activity of the oligomers. Thus, gallation of the dimer provides a dimer which is useful for the uses described in U.S. patent application Ser. No. 08/331,245 filed Apr. 2, 1997, now U.S. Pat. No. 6,297,273 issued Oct. 21, 2001.

We claim:

1. A process for preparing a benzyl-protected flavan-3-one of (+)-catechin comprises the steps of:
   (a) protecting the 5, 7, 3', and 4' phenolic hydroxyl groups of (+)-catechin with benzyl groups; and
   (b) oxidizing the benzyl-protected (+)-catechin of step (a) with Dess-Martin periodinane to form (2R)-5, 7, 3', 4'tetrakis(benzyloxy) flavan-3-one.

2. An alcohol inversion process for converting 5, 7, 3', 4'-[[tetra-O-benzyl (−)-catechin]]tetra-O-benzyl-(+)-catechin to 5, 7, 3', 4'-[[tetra-O-benzyl (−)-epicatechin]]tetra-O-benzyl-(−)-epicatechin comprises the steps of:
   (a) oxidizing 5, 7, 3', 4'-[[tetra-O-benzyl-(−)-catechin]] tetra-O-benzyl-(+)-catechin with Dess-Martin periodinane to form (2R)-5, 7, 3', 4'-tetrakis-(benzyloxy) flavan-3-one; and
   (b) reducing the protected flavan-3-one of step (b) with lithium tri-sec-butylborohydride in the presence of a Lewis acid to form the 5, 7, 3', 4'-tetra-O-benzyl-(−)-epicatechin.

3. A process for preparing (2R)-5, 7, 3', 4'-tetra-O-benzyl-(−)-epicatechin comprises the steps of:
   (a) protecting the 5, 7, 3', and 4' phenolic hydroxyl groups of (+)-catechin with benzyl groups;
   (b) oxidizing the alcoholic hydroxyl group at the 3-position of the protected (+)-catechin of step (a) with Dess-Martin periodinane to form (2R)-5, 7, 3', 4'-tetrakis (benzyloxy) flavan-3-one; and
   (c) reducing the protected flavan-3-one of step (b) with lithium tri-see-butylborohydride in the presence of a Lewis acid to form the (2R)-5, 7, 3', 4'-tetra-O-benzyl-(−)-epicatechin.

4. The process of claim 1 or 3, wherein the protecting step is carried out with benzyl bromide in the presence of sodium hydride.

5. The process of claim 4, wherein the (+)-catechin is dissolved in anhydrous dimethylformamide.

6. The process of claim 5, wherein the benzyl bromide is added dropwise at room temperature to a stirred suspension of the (+)-catechin and sodium hydride in anhydrous dimethylformamide.

7. The process of claim 1, 2, or 3, wherein the oxidizing step is carried out in moist methylene chloride.

8. The process of claim 1, 2, or 3, further comprising the step of purifying the (2R)-5, 7, 3', 4'-tetrakis (benzyloxy) flavan3-one by recrystallization from a chloroform/ether mixture.

9. The process of claim 2 or 3, wherein the reducing step is carried out with lithium-tri-sec-butylborohydride and a Lewis acid in tetrahydrofuran.

10. The process of claim 2 or 3, wherein the Lewis acid is anhydrous lithium bromide.

11. The process of claim 2 or 3, wherein the reaction mixture from the reducing step is treated with aqueous sodium hydroxide and then with aqueous hydrogen peroxide.

12. The process of claim 11, further comprising the step of adding ethanol to the reaction mixture.

13. The process of claim 12, further comprising the steps of dissolving the 5, 7, 3', 4'-[[tetra-O-benzyl-epicatechin]] tetra-O-benzyl-(−)-epicatechin in chloroform, separating an aqueous phase and a chloroform phase, extracting the aqueous phase with chloroform, combining the chloroform phases, and dying the combined chloroform phase to recover crude 5, 7, 3', 4'-tetra-O-benzyl-(−)-epicatechin.

14. The process of claim 13, further comprising the step of dissolving the crude 5,7,3',4'-tetra-O-benzyl-(−)-epicatechin in a mixture of boiling ethyl acetate and ethanol and allowing the 5,7,3',4'-tetra-O-benzyl-(−)-epicatechin to crystallize.

* * * * *

UNITED STATES PATENT AND TRADEMARK OFFICE
CERTIFICATE OF CORRECTION

PATENT NO. : 7,268,240 B2 Page 1 of 1
APPLICATION NO. : 10/858449
DATED : September 11, 2007
INVENTOR(S) : Romanczyk, Jr. et al.

It is certified that error appears in the above-identified patent and that said Letters Patent is hereby corrected as shown below:

On the Title Pg.
Please rewrite Item 60 so it reads as follows:

This application is a continuation of Serial No. 10/355,606 filed January 31, 2003, now pending which is a division of Serial No. 10/017,812 filed December 14, 2001, now U.S. Patent No. 6,528,664 issued March 4, 2003, which is a division of Serial No. 09/169,554 filed October 9, 1998, now U.S. Patent No. 6,420,572, which is a continuation-in-part of Serial No. 08/948,226, filed October 9, 1997, now U.S. Patent No. 6,207,842 issued March 27, 2001.

Col. 46 line 45 in Claim 2, at line 2, please delete "[[tetra-O-benzyl (-)-catechin]]"

Col. 46 line 46 in Claim 2, at line 3, please delete "[[tetra-O-benzyl (-)-epicatechin]]"

Signed and Sealed this

Seventh Day of April, 2009

JOHN DOLL
*Acting Director of the United States Patent and Trademark Office*